United States Patent
Xiao et al.

(10) Patent No.: US 10,328,259 B2
(45) Date of Patent: *Jun. 25, 2019

(54) TREATMENT OF BIOLOGICAL TISSUES USING SUBNANOSECOND ELECTRIC PULSES

(71) Applicant: OLD DOMINION UNIVERSITY RESEARCH FOUNDATION, Norfolk, VA (US)

(72) Inventors: Shu Xiao, Norfolk, VA (US); Andrei Pakhomov, Norfolk, VA (US); Karl H. Schoenbach, Norfolk, VA (US)

(73) Assignee: Old Dominion University Research Foundation, Norfolk, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/014,822

(22) Filed: Jun. 21, 2018

(65) Prior Publication Data

US 2018/0296837 A1    Oct. 18, 2018

Related U.S. Application Data

(63) Continuation of application No. 15/151,149, filed on May 10, 2016, now Pat. No. 10,029,093, which is a continuation of application No. 14/170,720, filed on Feb. 3, 2014, now Pat. No. 9,333,368.

(60) Provisional application No. 61/759,586, filed on Feb. 1, 2013.

(51) Int. Cl.
A61N 1/36 (2006.01)
A61N 2/00 (2006.01)
A61N 5/02 (2006.01)
A61N 1/40 (2006.01)

(52) U.S. Cl.
CPC .......... *A61N 1/36014* (2013.01); *A61N 1/40* (2013.01); *A61N 2/006* (2013.01); *A61N 5/02* (2013.01)

(58) Field of Classification Search
USPC .......................................... 607/139; 600/324
See application file for complete search history.

(56) References Cited

U.S. PATENT DOCUMENTS 6,432,050 B1 * 8/2002 Porat ................... A61B 5/0031
128/899
8,000,813 B2   8/2011 Schoenbach et al.
(Continued)

OTHER PUBLICATIONS

Attal, N., Cruccu, G., Haanpaa M., et al., "EFNS guidelines on pharmacological treatment of neuropathic pain," Eur J Neurol 13 1153-1169 (2006).
(Continued)

*Primary Examiner* — Nicole F Lavert
(74) *Attorney, Agent, or Firm* — Fish & Richardson P.C.

(57) ABSTRACT

A system for treatment of biological tissues is provided. The system can deliver electric pulses to a targeted region within a biological tissue. The system includes an antenna assembly and a lens. The antenna assembly is configured to generate and direct electromagnetic radiation. The lens is configured to be positioned between a surface of the biological tissue and the antenna assembly. The lens can have a plurality of lossy portions. The lens can be configured to be adjustable to create a patient-specific desired electric field distribution by selective positioning of the plurality of lossy portions within the lens.

20 Claims, 13 Drawing Sheets

(56) References Cited

U.S. PATENT DOCUMENTS

| | | | | |
|---|---|---|---|---|
| 2003/0011533 A1* | 1/2003 | Sakurada | ............... | H01Q 15/08 343/911 R |
| 2012/0283534 A1* | 11/2012 | Carr | ......................... | A61B 5/01 600/324 |
| 2013/0194540 A1* | 8/2013 | Pugh | ........................ | H01Q 1/22 351/159.03 |

OTHER PUBLICATIONS

Brown, J.A., "Motor cortex stimulation," Pain Medicine, 2006 vol. 7 No. S1.

Cruccu, G., Aziz, T. Z., Garcia-Larrea, L., Hansson, P. , Jensen, T. S., Lefaucheur, J.-P., Simpson, B. A. And Taylor, R. S., "EFNS guidelines on neurostimulation therapy for neuropathic pain," European Journal of Neurology 14, 952-970 (2007).

Rudiak, D. and Marg, E., "Finding the depth of magnetic brain stimulation: a reevaluation," Electroencephalogr. Clin. Neurophysiol. 93, 358-371(1994).

Jun, S. B., "Ultrasound as a Noninvasive Neuromodulation Tool," Biomed Eng Lett 2, 8-12, DOI 10.1007/s13534-012-0050-2 (2012).

Gavrilov, L.R., "Use of focused ultrasound for stimulation of nerve structures," Ultrasonics 22, 132-138 (1984).

Clement, G. T. And Hynynen, K., "A noninvasive method for focusing ultrasound through the human skull," Phys. Med. Biol. 47, 1219-1236 (2002).

Zhang, F. Gradinaru, V., Adamantidis, A.R., Durand, R., Airan, R.D., de Lecea, L. and Deisseroth, K., "Optogenetic interrogation of neural circuits: technology for probing mammalian brain structures," Nat Protoc. 5(3), 439-456 (2010).

Ryan, T. P., Trembly, B. S., Roberts, D. W., Strohbehn, J. W., Coughlin and C. T., Hoopes, P. J., "Brain hyperthermia: I. Interstitial microwave antenna array techniques—the Dartmouth experience, " Int J Radiat Oncol Biol Phys 29 (5), 1065-1078 (1994).

Dunn, D., Rappaport, C. M. and Terzuoli. Jr, A. J., "FDTD verification of deep-set brain tumor hyperthermia using a spherical microwave source distribution," IEEE Trans. MTT 44 (10), 1769-77 (1996).

Gouzouasis, I. A., Karathanasis, K. T., Karanasiou, I. S. and Uzunoglu, N. K., "Contactless passive diagnosis for brain intracranial applications: a study using dielectric matching materials," Bioelectromagnetics 31, 335-349 (2010).

Burfeindt, M. J., Zastrow, E. , Hagness, S. C., Van Veen, B. D. and Medow, J. E., "Microwave beamforming for non-invasive patient-specific hyperthermia treatment of pediatric brain cancer," 2011 Physics in Medicine and Biology 56, 2743-2754.

Xiao, S., Altunc, S., Kumar, P., Baum, C. E. and Schoenbach, K. H., "A reflector antenna for focusing in the near field," IEEE Antennas and Wireless Propagation Letters 9, 12-15 (2010).

Bajracharya, C., Xiao, S., Baum, C.E. And Schoenbach, K. H., "Target detection with impulse radiating antenna," IEEE Antennas and Wireless Propagation Letters vol. 10, 496-499 (2011).

Kumar, P., Baum, C. E., Altunc, S., Buchenauer, J., Xiao, S., Christodoulou, C. G., Schamiloglu, E. and Schoenbach, K. H., "A hyperband antenna to launch and focus fast high- voltage pulses onto biological targets," IEEE Trans. on Microwave Theory and Tech., 2011 59(4), 1090-1101.

Altunc, S, Baum, C.E., Christodoulou, C.G., Schamiloglu, E. and Buchenauer, C. J., "Focal waveforms for various source waveforms driving a prolate- spheroidal impulse radiating antenna (IRA)," Radio Sci. 43: RS4S13 (2008).

Lazebnik M, Popovic D, McCartney L, Watkins CB, Lindstrom MJ, Harter J, Sewall S, Ogilvie T, Magliocco a, Breslin ATM, Temple W, Mew D, Booske JH, Okoniewski M, Hagness SC., A large-scale study of ultrawideband microwave dielectric properties of normal, benign and malignant breast tissues obtained from cancer surgeries, Phys. Med. Biol. 52, 6093-6115 (2007).

Gabriel C, 2007. Dielectric Properties of Biological Material. Handbook of Biological Effects of Electromagnetic Fields, 3rd Edition, Edited by F. S. Barnes and B. Greenebaum, CRC press.

Lin JC, Bernardi P. 2007. Computational methods for predicting field intensity and temperature change. In Barnes FS, Greenebaum B (eds): Handbook of Biological Effects of Electromagnetic Fields, 3rd Edition, Edited by, CRC.

Baum CE. 2007. Focal waveform of a prolate-spheroidal impulse-radiating antenna (IRA). Radio Sci. 42: RS6S27.

Rogers WR, Merritt JH, Comeaux JA Jr., Kuhnel CT, Moreland DF, Teltschik DG, Lucas JH, Murphy MR. 2004. Strength-duration curve for an electrically excitable tissue extended down to near 1 nanosecond. IEEE Transactions on Plasma Science 32(4):1587-1599.

Jauchem JR, Seaman RL, Lehnert HM, Mathur SP, Ryan KL, Frei MR, Hurt WD. 1998. Ultra-wideband electromagnetic pulses: lack of effects on heart rate and blood pressure during two-minute expo sure so f rats. Bio electromagnetics.19 :330-333.

Jauchem JR, Frei MR, Ryan KL, Merritt JH, Murphy MR. 1999. Lack of effects on heart rate and blood pressure in ketamine-anesthetized rats briefly exposed to ultra-wideband electromagnetic pulses. IEEE Trans. Biomed. Eng. 46 (1):117-120.

Miller SA, Bronson ME, Murphy MR. 1999. Ultrawideband radiation and pentylenetetrazol-induced convulsions of rats. Bioelectromagnetics 20: 327-329.

Walters TJ, Mason PA, Sherry CJ, Steffen C, Merritt JH. 1995. No detectable bioeffects following acute exposure to high peak power ultra-wide band electromagnetic radiation in rats. Aviat. Space Environ. Med.66: 562-567.

Sherry CJ, Blick DW, Walters TJ, Brown GC, Murphy MR.1995. Lack of behavioral effects in nonhuman primates after exposure to ultrawideband electromagnetic radiation in the microwave frequency range. Radiat. Res. 143(1): 93-97.

Pakhomova ON, Belt ML, Mathur SP, Lee JC, Akyel Y. 1988. Ultra-wideband electromagnetic radiation does not affect UV-induced recombination and matagenesis in yeast. Bioelectromagnetics 19:128-130.

Jiang N, Cooper by. 2011. Frequency-dependent interaction of ultrashort E-fields with nociceptor membranes and proteins. Bioelectromagnetics 32:148-163.

Altunc S, Baum CE, Christodoulou CG, Schamiloglu E, Buchenauer CJ. 2009. "Design of a special dielectric lens for concentrating a subnanosecond electronmagnetic pulse on a biological target" IEEE 16(5) 1364-1375.

Pham DT, Karaboga D. 2000. Intelligent Optimisation Techniques. Springer, London.

Baum CE, Baker WL, Prather WD, Lehr JM, O'Loughlin JP, Giri DV, Smith ID, Altes R, 10 Fockler J, McLemore D, Abdalla MD, Skipper MC. 2004. JOLT: a highly directive, very intensive, impulse-like radiator. Proceedings of the IEEE 92(7):1096-1109.

Vitek JL, DeLong MR, Starr PA, Hariz MI, Metman LV. 2011. Intraoperative neurophysiology in DB S for dystonia. Movement Disorders 26(S1): 35-40.

Euler L, "Optimization Techniguqes: an overview" Adaptation, Learning, and Optimization 15,DOI: 10.1007/978-3-642-37846-1_2, pp. 13-44 (2014).

* cited by examiner

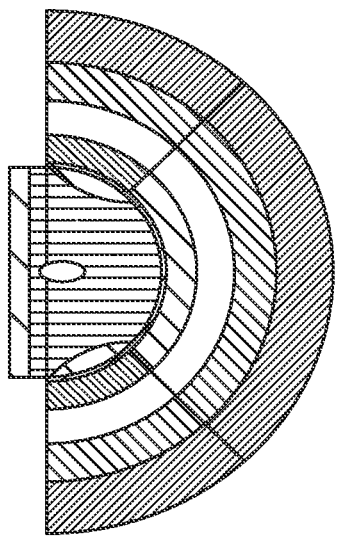 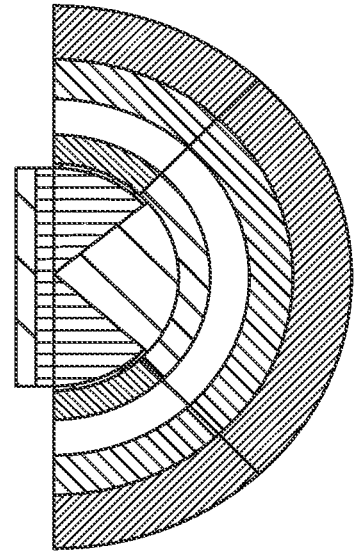
FIG. 13A  FIG. 13B
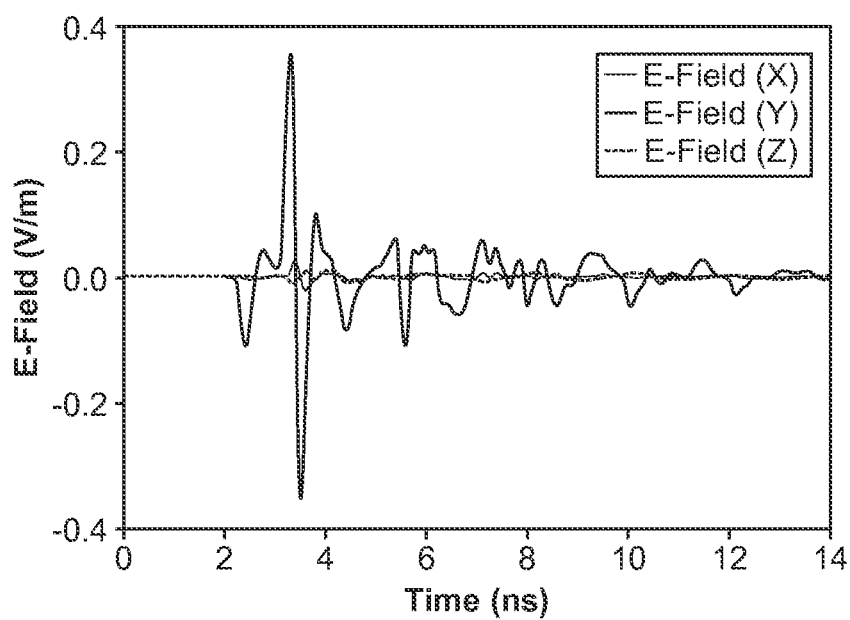
FIG. 14

TREATMENT OF BIOLOGICAL TISSUES USING SUBNANOSECOND ELECTRIC PULSES

CROSS-REFERENCE TO RELATED APPLICATION

This application is a continuation of U.S. application Ser. No. 15/151,149, filed on May 10, 2016, published as U.S. 2017-0095664 A1, now a U.S. Pat. No. 10,029,093, which is a continuation of U.S. application Ser. No. 14/170,720, filed on Feb. 3, 2014, published as U.S. 2014-0222126 A1, now a U.S. Pat. No. 9,333,368, which claims priority to Provisional Application Ser. No. 61/759,586, filed on Feb. 1, 2013. The entire contents of all of the above-identified applications are incorporated herein by reference as if fully set forth herein.

GOVERNMENT LICENSE RIGHTS

This invention was made with government support under contract no. FA95500810191 awarded by the U.S. Air Force Office of Scientific Research (AFOSR). The government has certain rights in the invention.

FIELD OF THE INVENTION

The present invention relates to neurostimulation, and more specifically to apparatus and methods for treatment of biological tissues using subnanosecond electric pulses.

BACKGROUND

Neurostimulation has been increasingly used as a therapy in areas where conventional pharmacological approaches become ineffective, such as in treating refractory pain, Parkinson disease, dystonia, and obsessive compulsive disorder. The stimulated structures may vary greatly. For example, in treating neuropathic pain, the neurostimulation techniques include transcutaneous electrical nerve stimulation (TENS), peripheral nerve stimulation (PNS), nerve root stimulation (NRS), spinal cord stimulation (SCS), deep brain stimulation (DBS), epidural motor cortex stimulation (MCS), and repetitive transcranial magnetic stimulation (rTMS)[1]. A specific example is using MCS to treat trigeminal neuropathic facial pain, a syndrome of severe, constant pain due to pathological change or injury to the trigeminal system[2]. The target is located anterior to the central sulcus and posterior to the splitting of the inferior frontal sulcus.

Most neurostimulation methods are invasive and rely on electrodes that are implanted into the stimulated structure through intraoperative surgery. A pulse generator and a battery must be implanted in the body, often causing complications such as infection, lead migration, hardware malfunction, battery failure or unwanted stimulations. It was reported that, overall, 43% of patients experience one or more complications[3]. Significant research has been conducted on the use of rTMS, a non-invasive approach for brain stimulation. In rTMS, electric fields are induced by a fast changing, magnetic flux to cause the stimulation. The electric field penetration depth is limited to a 2 $cm^4$, and the excitable volume is not less than ten cubic centimeters[5]. Besides electrical stimulation, ultrasound energy was used for neurostimulation studies[6], aiming to improve the focus of the stimulation and to access deeper brain zones, but the significant difference in the sonic properties between the brain tissue and the bone, as well as the irregular skull shape prevent the focusing of the power[7]. Recently, optogenetic approaches revolutionized the neurostimulation using light, but the expression of photon-sensitive ion channels is required and the implantation of a light source is needed[8].

SUMMARY

Embodiments of the invention concern systems and methods for the treatment of biological tissues. In a first embodiment of the invention, a system for treatment of biological tissues is provided. The system can deliver electric pulses to a targeted region within a biological tissue. The system includes an antenna assembly and a lens. The antenna assembly is configured to generate and direct electromagnetic radiation. The lens is configured to be positioned between a surface of the biological tissue and the antenna assembly. The lens can have a plurality of lossy portions. The lens can be configured to be adjustable to create a patient-specific desired electric field distribution by selective positioning of the plurality of lossy portions within the lens.

In some examples, the lens can comprise a plurality of layers. Each layer can have a different value of conductivity. The plurality of lossy portions can be positioned within a single layer of the plurality of layers.

In some examples, the plurality of lossy portions can be positioned within multiple layers of the plurality of layers.

In some examples, the plurality of lossy portions can be positioned at various incident angles of the lens.

In some examples, each of the plurality of lossy portions can be configured to attenuate a portion of the electromagnetic radiation traveling in at least one direction.

In some examples, the targeted region can be a deep tissue region of the biological tissue. The system can be configured to increase a transmission of the electromagnetic radiation to the deep tissue region of the biological tissue. A focal spot in the deep tissue region can be generated by attenuating the electric fields on or near a z-axis.

In some examples, the deep tissue region can comprise a region of 6 to 8 centimeters (cm) below a surface of the biological tissue.

In some examples, the system configuration can simultaneously target both deeper and shallower regions of the biological tissue.

In some examples, the electromagnetic radiation from the antenna assembly can be configured to enter the targeted tissue at wide angles. The wide angles can be equal or greater than 45 degrees.

In some examples, the antenna assembly can comprise a wide-band antenna configured to provide wide and narrow angles.

In some examples, the system ca n further comprise a pulse generator coupled to the antenna assembly and configured for generating a series of pulses. The pulse generator can be configured for generating a pulse having a pulse duration of less than or equal to 1 ns. Alternatively, or in addition, the pulse generator can be configured for generating a pulse having a magnitude between about 1 kV and 1 MV and a repetition rate between about 1 Hz and 1 MHz.

In some examples, at least one of a rise time or a fall time of the electric pulses can be from 1 ps to 1 ns.

In some examples, the lens can comprise a plurality of layers and at least one of a radius, thickness, or dielectric constant of each layer of the plurality of layers varies.

In some examples, the antenna assembly can comprise an antenna configured for receiving the electric pulses and generating the electromagnetic radiation and a reflector configured for directing the electromagnetic radiation to the lens.

In some examples, the lens can be shaped and can be configured for positioning adjacent to the biological tissue. A dielectric constant of a surface of the lens that is adjacent to the biological tissue can substantially match a dielectric constant of the biological tissue.

BRIEF DESCRIPTION OF THE DRAWINGS

FIG. 13A schematically shows the case where a partially lossy lens is used and the distribution of electric field in the target shows a focal point formed in the deep zone of the target and two hot spots on the target surface;

FIG. 13B schematically shows the case where a non-lossy lens is used and the electric field distribution in the hemispherical tissue can be schematically depicted in a pie shape;

FIG. 14 is a plot of the pulse waveform at the 6 cm depth on the z-axis in the brain exposed to a reflector antenna;

DETAILED DESCRIPTION

Figures 1A, 1B:
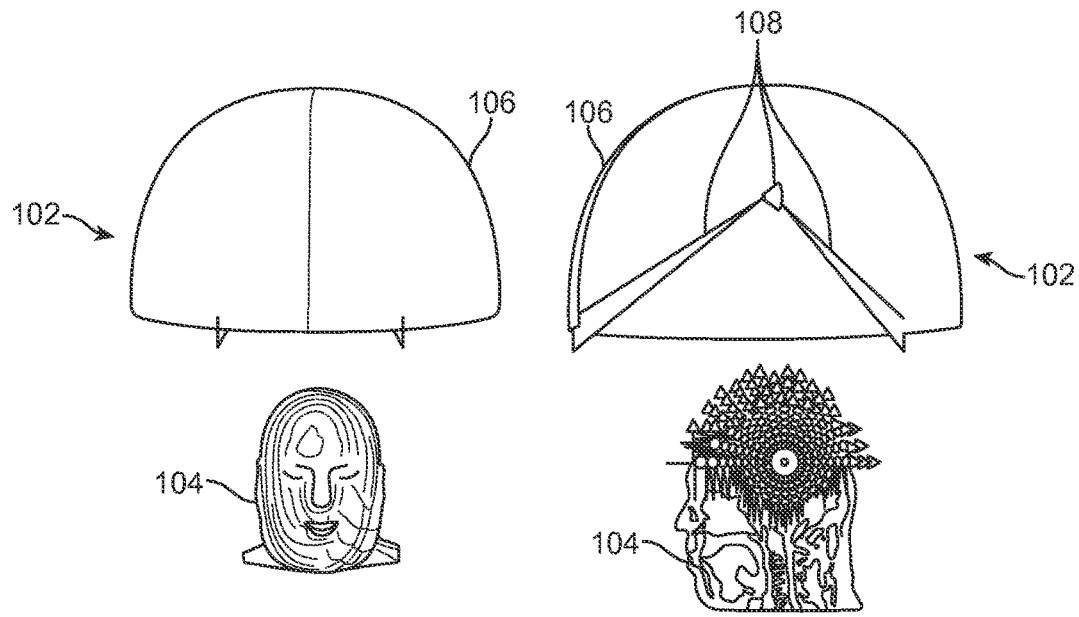
FIGS. 1A and 1B show front and side views of an arrangement of an antenna assembly with respect to a head of a patient without a lens in accordance with the various embodiments.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

In view of the limitations of conventional neurostimulation systems and methods, the present invention provides a new neurostimulation method using intense, high power, subnanosecond electric pulses (psEP) as stimuli. In some embodiments, such electric pulses can be delivered by ultrawideband antennas in the form of electromagnetic waves, which have the potential to penetrate deeper with a higher resolution. For example, a 200 ps subnanosecond electric pulse contains wideband frequencies up to 5 GHz, according to the reciprocal relation between pulse duration and frequency. Previous numerical and experimental studies suggest it is possible to focus high frequency radiation using an antenna array. In a brain hyperthermia study, the array of four dipole antennas spaced 2.0 cm apart was capable of heating a volume of 5.9 cm×2.8 cm×2.8 cm[9]. Dunn et al.[10] showed that careful selection of the source electric field distribution around the entire surface of the head can generate a well resolved focus. Gouzouasis et al.[11], in a deep brain monitoring system, showed electric fields at 1.1 GHz that are radiated from a discone antenna together with an ellipsoidal reflector can be focused on the center of the head. A beamforming approach was shown to focus 1 GHz microwave radiation through constructive interference to treat brain cancer by Burfeint et al.[12] in a modeling study.

However, a significant issue with such conventional treatment methods is whether or not there is sufficient transmission, to the tissues of interest inside a patient's head, of pulse radiation resulting from subnanosecond electric pulses (psEPs). This is described with respect to FIGS. 1A and 1B. FIGS. 1A and 1B show front and side views of an arrangement of an antenna assembly 102 with respect to a head of a patient 104. As shown in FIGS. 1A and 1B, the antenna assembly 102 consists of an ellipsoidal or prolate spheroid reflector 106 and a discone antenna 108. In such a configuration, although the pulse radiation would be delivered to the patient 104, the psEPs may not penetrate the patient in an amount sufficient for therapeutic purposes due to reflection losses and incident angles. For example, if the pulses are sent from the air to a tissue which has a dielectric permittivity of 80, about 80% of the electric field is reflected due to the large contrast of dielectric property.

Thus, another aspect of the various embodiments is to provide a configuration that increases the transmission of pulse radiation from psEPs to the regions of interest in the brain. First, to increase the transmission of radiation to deep tissues, the pulse radiation from the reflector antenna is configured so as to enter the tissue at wide angles. Secondly, the reflection loss due to the abrupt change in tissue permittivity at the interface of air and tissue is minimized. Thus, the various embodiments utilize a combination of a wideband antenna, capable of wide and narrow angles, and an inhomogeneous, partially lossy dielectric lens. An exemplary arrangement for such a configuration is illustrated in FIGS. 2A and 2B.

Figures 2A, 2B:
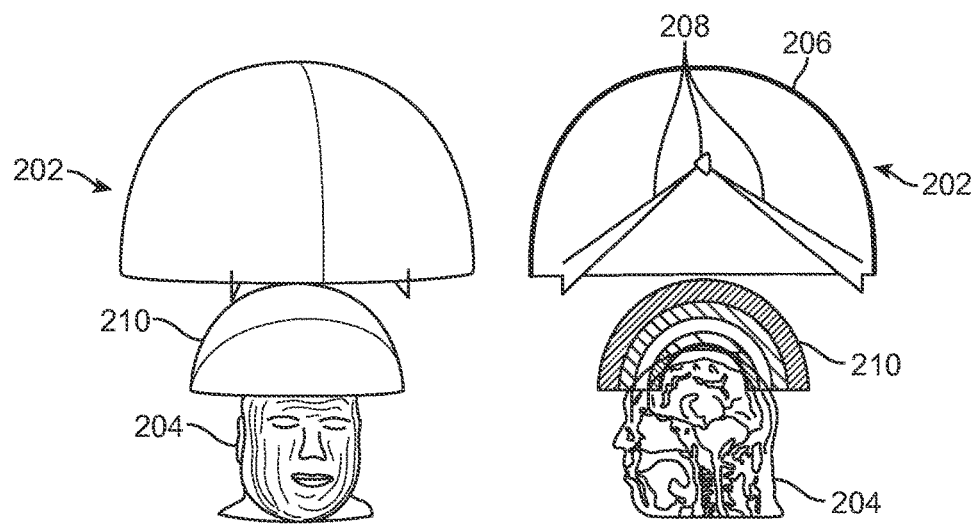
FIGS. 2A and 2B show front and side views of an arrangement of an antenna assembly with respect to a head of a patient with a lens in accordance with the various embodiments.

FIGS. 2A and 2B show front and side views of an arrangement of an antenna assembly 202 with respect to a head of a patient 204. As shown in FIGS. 2A and 2B, the antenna assembly 202 consists of an ellipsoidal or prolate spheroid reflector 206 and a discone antenna 208, similar to the configuration of FIGS. 1A and 1B. However, the arrangement in FIGS. 2A and 2B further includes an inhomogeneous, partially lossy dielectric lens, specifically a multilayer lens 210 to match the impedance from air to tissue. This is illustrated with respect to FIG. 3.

Figure 3:
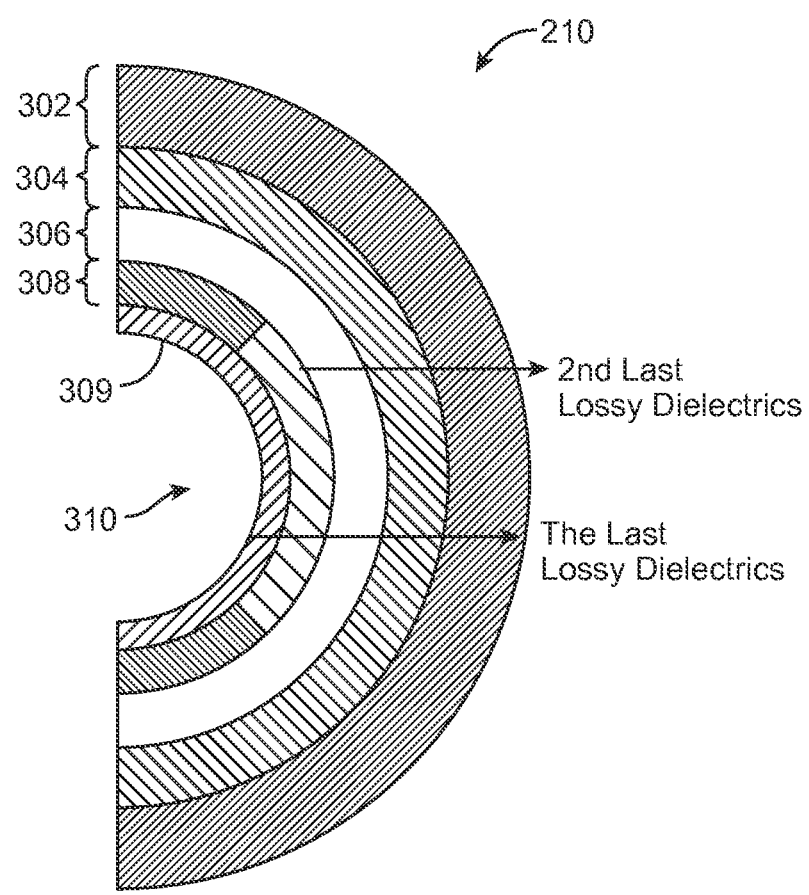
FIG. 3 shows a cutaway view of an exemplary configuration for lens in FIGS. 2A and 2B.

FIG. 3 shows a cutaway view of an exemplary configuration for lens 210 in FIGS. 2A and 2B. In some embodiments, as illustrated in FIG. 3, the lens 210 can be configured as a hollow, hemispherical or substantially hemispherical with a hemispherical or substantially hemispherical cavity 310. As used herein, the term "substantial" or "substantially" refer to being within 20% of the stated value or property.

The cavity 310 can be used to locate the lens 210 around tissues. Thus, the cavity 310 (and the lens 210) can be sized in accordance with the tissues to be treated. For example, the cavity can be configured to be placed on and over a portion of a patient's head, as shown in FIGS. 2A and 2B. In another example, the cavity can be configured to be placed over a female breast. In such a configuration, the cavity 310 can have a radius corresponding to the size of the breast of the patient. However, the various embodiments are not limited in this regard and the lens and cavity size can vary in the various embodiments.

As further shown in FIG. 3, the lens 210 can be defined using five layers, layers 302, 304, 306, 308, and 309, of different dielectric materials, where each layer has a hollow, hemispherical or substantially hemispherical shape. The dielectric materials and their order in lens 210 can be selected so that the dielectric constant from varies in substantially monotonic profile. In some embodiments, this can be an exponential profile. The exponential profile can range from a dielectric constant of air or other ambient to a dielectric constant of the tissues in cavity, $\varepsilon_{rmax}$. Due to the increase of the dielectric constant provided by such a configuration, the focal spot size can be reduced by a factor of $\varepsilon_{rmax}^{-1/2}$ at the innermost layer, and the electric field can be enhanced by a factor of $\varepsilon_{rmax}^{1/4}$. In the various embodiments, the configuration of lens 210 can be selected in a manner similar to that described by Altunc et al. in "Focal waveforms for various source waveforms driving a prolate-spheroidal impulse radiating antenna (IRA)," Radio Sci. 43: RS4S13 (2008). However, in the various embodiments, the lens 210 is configured with two major differences. First, Altunc et al. describe a lens with five (5) layers and no cavity. That is a solid hemispheric ally shaped lens. In contrast, the lens 210 is configured such that the patient's tissues define the inner most the innermost layer of the lens, as described above. Second, the innermost layers 308, 309 of the lens 210 are configured to be lossy for angles below 45°. This means that for azimuth angles between −45° and +45°, the lens 210 has a finite conductivity (2 S/m).

As noted above, the radius, thickness, and dielectric constant of each of layers 302-309 can vary. In one particular, configuration, the thicknesses of layers 302, 304, 306, 308, and 309 can be 3 cm, 2.3 cm, 1.9 cm, 1.6 cm, and 0.2 cm, respectively. The dielectric constants of these layers are 1.6, 2.4, 3.7, 5.8, and 9.0, respectively. The innermost layer, layer 309 is selected to have a dielectric constant approximately equal to the dielectric constant of the biological tissue in the cavity. In some embodiments, the radius of the cavity can vary from a few centimeters (1-3 cm) to approximately 10 cm (8-12 cm), where the radius is selected in accordance with the tissues and structures in the cavity. However, other radii outside this range can be provided. As noted above. The materials for the lens can be the composite of nanometer-sized metal oxides, polymers, or ceramics, which have the dielectric permittivity close to the tissue value. Some liquids, such as corn syrup, can be used in a gel form and work as the innermost layer of the lens.

In an alternate embodiment, the lens can include one or more lossy elements along radial directions. These lossy elements can be selected so as to attenuate the electromagnetic radiation in at least one pre-defined radial path to control the angle of the power incidence.

Figure 4:
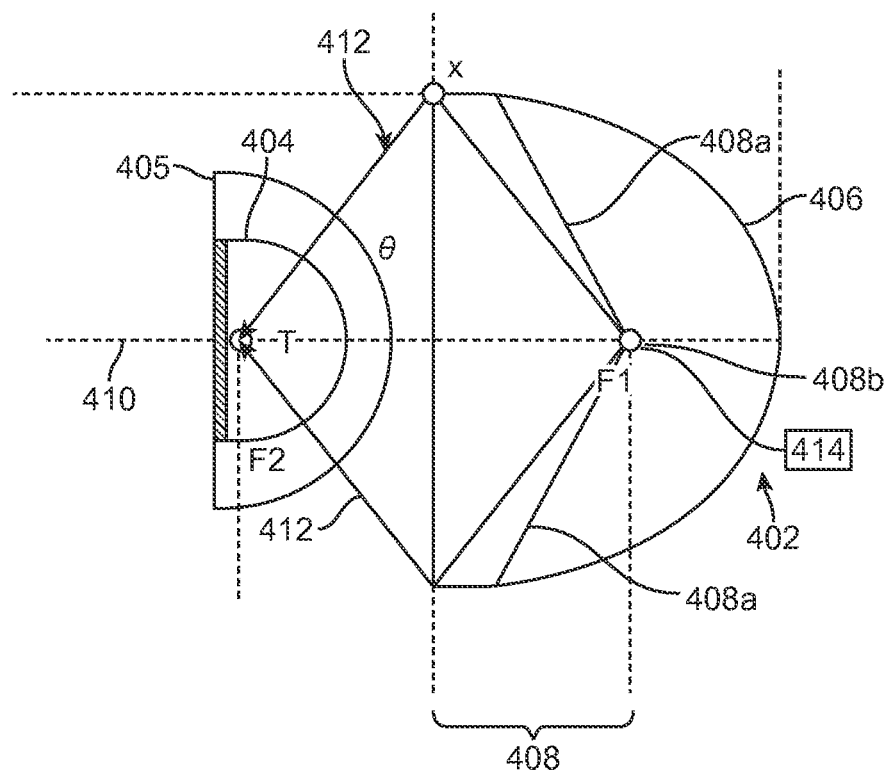
FIG. 4 schematically shows an arrangement of an antenna assembly and hemispherical shaped tissues to be treated in accordance with the various embodiments.
Figure 5:
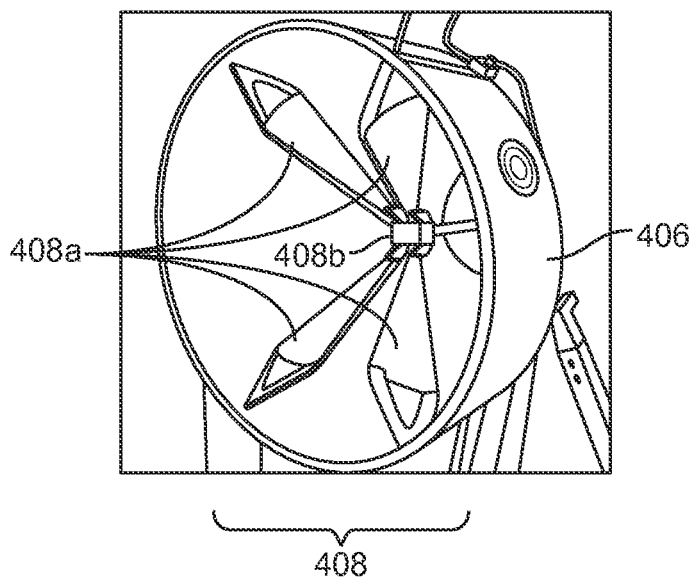
FIG. 5 is a more detailed view of the antenna assembly of FIG. 4.

As shown in the configuration of FIGS. 2A and 2B, the antenna assembly 202 consists of a reflector 206 and a discone antenna 208. However, the various embodiments are not limited to solely this configuration. As noted above, the primary requirement with respect to the pulse radiation is that such radiation enters the patient's tissues at wide angles. This is illustrated with respect to FIGS. 4 and 5. FIG. 4 schematically shows an arrangement of an antenna assembly 402 and hemispherical shaped tissues 404 to be treated. FIG. 5 is a more detailed view of the antenna assembly.

In FIGS. 4 and 5, the antenna assembly 402 consists of an ellipsoidal reflector 406 and a discone antenna 408. The discone antenna 408 consists of vanes 408a defining a cone and a disc 408b to which a signal from a pulse generator (not shown) is fed. The disc 408b is positioned at a first focal point (F1) of the reflector 402 and the target tissues are positioned at a second focal point (F2) of the reflector 402, such that the hemispherical shaped tissues, i.e., the patient 404, a lens 405, the disc 408b, the vanes 408a, and the reflector 402 are placed so that they are substantially symmetric with respect to an axis 410 defined by the focal points F1 and F2.

In order to provide wide angle for the patient's tissues, the reflector 406 is configured so that pulse radiation from focal point F1 impinging on edge X of reflector 406 is reflected toward focal point F2 so that an angle θ with respect to axis 410 is greater than 45 degrees. Such configuration can be utilized for directing and focusing pulse radiation at focal points deep within the hemispherical shaped tissues of the patient 404 to be treated. However, the present disclosure contemplates that in some configurations, it shallower tissues may need to be treated. In such configurations, the reflector 406 can be configured to provide an angle θ less than 45 degrees.

In operation, the system described above is utilized as follows. First, the patient 404 and the dielectric lens 405 are positioned, with respect to the antenna assembly 402, in the manner described above. In particular, as described above, the patient is positioned such that the target area T within the patient 404 to be treated (e.g., area within the head of patient 404) is positioned at the second focal point of the reflector of the antenna assembly. Once positioned, a pulse generator 414 can be utilized to generate the psEPs.

In the various embodiments, the actual width of the psEP can vary. For example, the pulse widths can be between about 1 ps and 1 ms. However, of greater importance in the various embodiments, with respect to neurostimulation, is the transient of such pulses, i.e., the width of the rise time and the fall time of such pulses, which can be 1 ps to 1 ns. That is, the useful portion of the electromagnetic radiation being generated is the high frequency component associated with the transitions in the pulse sequence. Such pulse transients are capable of being radiated by antennas of 1 meter or less. In particular, the transient of such pulses are important since the length of the transient can affect whether or not neurons shut down. Specifically, the power delivered to biological tissues for treatment will vary as the transient varies. Thus insufficient stimulation may be provided. For example, if the transients are too long, the power delivered is spread out and cannot be accurately focused in a single area. In some embodiments, the psEPs can be configured to have a transient be between about 1 ps to 1 ns, such as 100-500 ps, or 200 ps. These pulses can have voltages between about 1 kV and 1 MV. These provide electric fields magnitudes between about 1 V/cm to 1 MV/cm, such as between about 1 kV/cm to 500 kV/cm, or 100 kV/cm.

In some embodiments, the pulses can be delivered as series of consecutive pulses. This allows for the accumulation of depolarization in neurons before action potentials fire. In these embodiments, the pulses can have a repetition rate between about 1 Hz to 1 MHz. In some configurations, where additional neurostimulation is required, the repetition rate is increased while maintaining the transient of the pulses constant.

It should be noted that the configuration of the antenna assembly illustrated in the preceding figures is provided solely for illustrative purposes and not by way of limitation. Rather, the present disclosure contemplates that the pulse radiation to be delivered to hemispherical shaped tissues via a hemispherical lens can be generated and delivered in a variety of ways. That is, the antenna assembly can include any type of antenna for generating pulse radiation based on psEPs and any type of reflector, lens, or directing device for directing the pulse radiation at the desired angles. Other suitable antenna configurations include, such as a resistive-loaded dielectric rod or dipole antenna, an antenna array which includes a number of antennas, or a resistance terminated transmission line antenna.

Other exemplary antenna assemblies suitable for the various embodiments are described in U.S. Pat. No. 8,000,813, the contents of which are herein incorporated by reference in their entirety.

Although the various embodiments have been described primarily with respect to neurostimulation, the present invention is not limited in this regard. In some embodiments, the psEPs and resulting pulse radiation can be configured for other therapeutic purposes. For example, the systems and methods described herein can be adapted for purposes of inducing cell death in tissues of interest. Alternatively, the methods described herein can be adapted for purposes of increasing cell membrane permeability to allow for the delivery of therapeutic agents inside cells. These agents can include chemical or pharmacological agents and biological agents for treatment of cells or inducing cell death.

Further, although the various embodiments have been described generally with respect to a lens positioned on top of a hemispherically shaped body part, such as female breast or a head, the various embodiments are not limited in this regard. Rather, the systems and methods described herein can be utilized for placing the lens on any body part to treat any type of biological tissue. In the various embodiments, this can be accomplished in a variety of ways. In some embodiments, the inner layer of the lens can be molded to fit the non-hemispherically shaped body part. In other embodiments, the non-hemispherically shaped body part can be placed in the cavity with a gel, liquid, or solid mold with a similar dielectric constant to provide a hemispherically shaped object in the cavity. Similarly, other non-hemispherically shaped biological tissues can be used in a similar fashion.

Examples

The following examples are provided solely for illustrating various aspects of the present invention and should not be considered limiting in any way.

The following study is based on the inclusion of a hemispherically shaped tissue as the target in the antenna configuration. This study is directed to the varying of the electrical properties (permittivity and conductivity) of the tissue and thereafter examining the spatial distribution of the electric field intensity in the target, particularly in the deep region, which is defined as 6-8 cm below the surface. Further, the temporal development and the spatial distribution of the electric field intensity in a human brain is also examined, with the aim of determining the electric pulse parameters required for deep brain stimulation[32]. In particular, the study was directed to answering the following questions:

1. How deep can the subnanosecond pulses penetrate and still achieve a reasonable confinement of the electric field distribution?
2. Can one use one antenna to focus pulsed radiation into tissue?
3. What spatial resolution can such antenna provide?

To answer these questions, 3-D electromagnetic simulation software, CST MICROWAVE STUDIO, available from CST of America, Inc. of Framingham, Mass., has been used. The transient solver based on Finite Integration Technique (FIT) is used for the time domain simulation. The human model is a HUGO human body model, also available from CST of America, Inc. of Framingham, Mass., which has a resolution of 1 mm×1 mm×1 mm.

Figure 6:
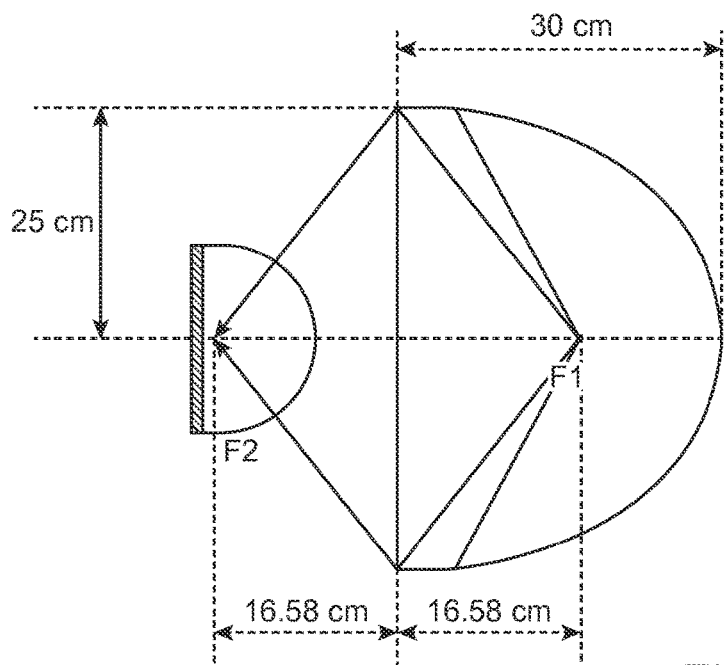
FIG. 6 is a schematic of a spatial arrangement of components in accordance with an exemplary embodiment of the invention.

For this study, the basic configuration (reflector antenna and target) used in this modeling study are substantially similar to that shown and described above with respect to FIGS. 2A, 2B, 4, and 5. The antenna has a prolate spheroid reflector fed by a TEM conical transmission line starting from the first focus as a wave launcher or disc. The reflector is one half of a prolate spheroid with the minor axis on the aperture plane. The geometry of the antenna was taken from an existing antenna[13], constructed by Fan Research of Albuquerque, N. Mex. The features of the antenna include:

linearly polarized radiation, broadband radiation, and high power capability. The radiation at the second focus is vertically polarized, which is the mirror image of the electric field at the starting point of the transmission line fed by a differential input. Dimensions utilized for this study are shown in FIG. 6.

A lens was used in conjunction with the impulse radiating antenna, aiming to improve the coupling of the EM energy to tissue, as discussed above with respect to FIG. 3. The lens is made of multiple layers with dielectric permittivity varying according to an exponential profile in order to allow for a maximum transmission[29]. The innermost layer has the same dielectric constant as the targeted tissue.

Figure 7A:
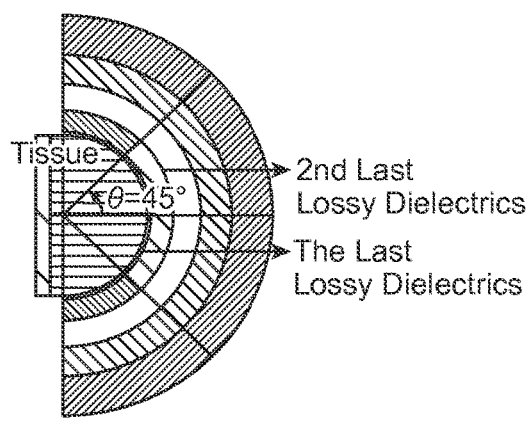
FIG. 7A shows the dielectric lens consisting of five layers is used in conjunction with the reflector antenna of FIG. 6 and hemispherical shaped tissues.

In the simulation, a tissue target was used that has a hemispherical shape, as shown in FIG. 7A. FIG. 7A shows dielectric lens consisting of five layers is used in conjunction with the reflector antenna. The last layer of the lens is adjacent the biological tissue. The biological tissue has radius of 6.0 cm. The dielectric constants of these five layers from the outermost to the innermost are 1.6, 2.4, 3.7, 5.8, and 9.0, respectively. The biological tissue (innermost layer) has the same dielectric constant as the 5th layer.

Such shape was chosen because the spherically incoming waves from the reflector antenna have the same phase along the circumference of the tissue, which results in a maximum field at the second focus for the same optical path. The relative permittivity of muscle and fat tissue is on the order of 45 (for muscle) and 5 (for fat). Their conductivity is in the range of 0.1-2 S/m. The values could vary for real tissues[17]. The dielectric properties are dependent on the frequency, which can be described by the second order Debye model[18]. This type of model is not available in the software, so not included are the effects of dispersion. The dispersion of the dielectrics in general broadens the pulse waveforms and lowers the pulse intensity, the results of the simulation without dispersion loss therefore serves as the best-scenario estimate of the pulse delivery in terms of pulse intensity and focal spot size.

Figure 7B:
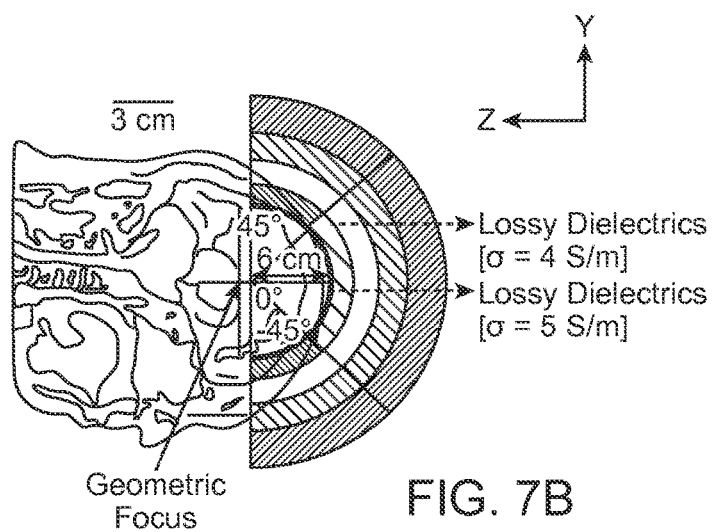
FIG. 7B shows the dielectric lens consisting of five layers is used in conjunction with the reflector antenna of FIG. 6 and a patient head.

In addition to the hemispherical target, the HUGO human body model was used to determine the temporal and spatial distribution of the pulsed electric fields in a human brain, as shown in FIG. 7B. In the human head model used in this study, the dielectric constants and conductivities of the tissues considered in this study are: bone ($\varepsilon_r$=11.78, $\sigma$=0.28), gray matter ($\varepsilon_r$=50, $\sigma$=1.39), fat tissue ($\varepsilon_r$=5.35, $\sigma$=0.08), nervus opticus ($\varepsilon_r$=30.87, $\sigma$=0.84), white matter ($\varepsilon_r$=37, $\sigma$=0.91) and skeletal muscle ($\varepsilon_r$=55.33, $\sigma$=1.44). The heterogeneity of the tissues may cause multiple reflections and reduce the transmission of the electromagnetic wave energy. In this study, focus is on the attenuation of the pulse in the brain, the size of the focal volume and the required input pulse parameters to create the electric fields that are at the level of inducing any biological effects. It should be noted that the accuracy of the CST software is satisfactory. As reported previously[15], using the same software to simulate the impulse radiating antenna gave results very close to the measurement results. One can therefore assume that the simulation yield is sufficiently accurate in predicting the effect of wideband pulses on a human brain.

The electromagnetic waves emitted from the prolate spheroid reflector are spherical waves, converging at the second geometric focus of the reflector. The phases of the incoming spherical waves on the circumference of the target are identical. Because the electric fields of the converging spherical waves are parallel to the surface of the hemispherical tissue, the transmittance into the tissue is optimum[19]. In the simulation, the relative permittivity of the tissue has been varied from a value of 9 to a value of 70, and the conductivity was also varied from 0 to 0.5 S/m. Zero conductivity corresponds to a lossless tissue. The tissue conductivity near 0.5 S/m is close to that of breast tissue[17].

Figure 8A:
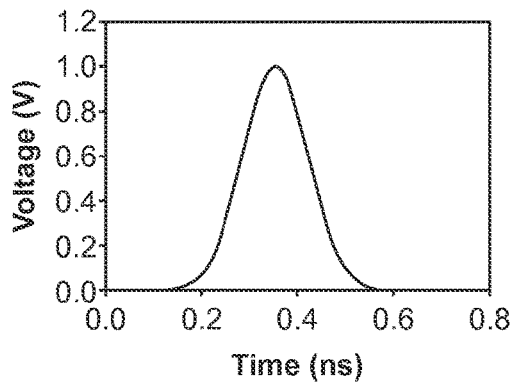
FIG. 8A shows a plot of a Gaussian pulse used in the various embodiments.
Figure 8B:
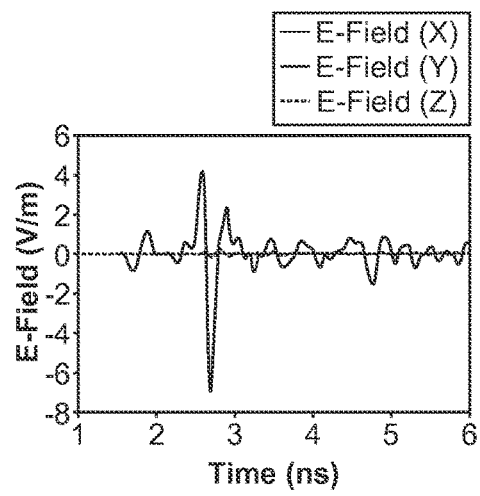
FIG. 8B shows a plot of the electric field pulse at a focal point as a function of time.

Input Gaussian pulses (with a 200 ps transient) were fed into the antenna. A schematic of such a pulse is shown in FIG. 8A. For a relative permittivity of $\varepsilon_r$=9 and a conductivity of the target of $\sigma$=0, the electric field was sampled along the z-axis from the tissue surface to the geometric focus of the reflector, which is 6 cm deep. The electric field pulse at the focal point is shown in FIG. 8B. This electrical field pulse consists of prepulse and an impulse. The prepulse reaches the second focal point at an approximate time, t=27.16/30+6*($\sqrt{9}$)/30=1.505 ns. The electric field pulse reflected from the prolate spheroid reflector surface converges at the second focal point $F_2$. This constitutes the impulse part of the wave at the focal point and occurs at approximately t=54/30+6*($\sqrt{9}$)/30=2.4 ns. The shape of the impulse is close to the time derivative of the Gaussian wave form[20]. The electric field component that contributes mostly to the electric field at the focal point is the y-component. The amplitudes in x and z direction are negligible.

Figure 9A:
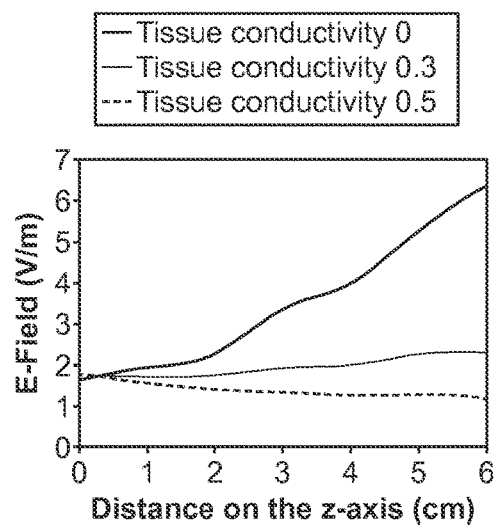
FIG. 9A shows a plot of the electric field distribution on the z-axis for different tissue conductivities.
Figure 9B:
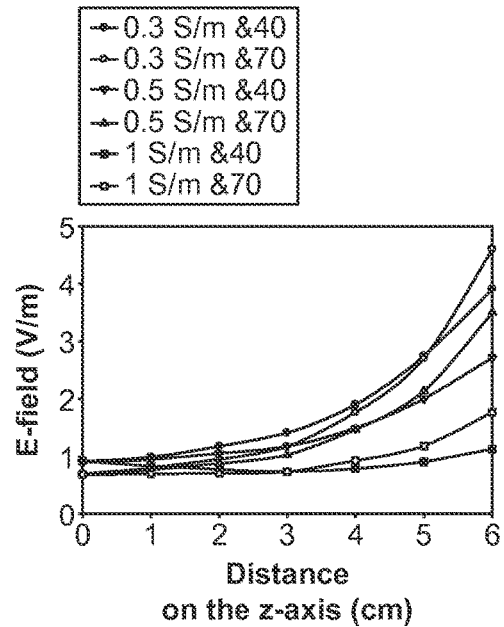
FIG. 9B shows a plot of the electric field distribution for higher tissue dielectric permittivity.

In FIG. 9A, the electric field distribution on the z-axis for different tissue conductivities (s) is shown. The tissue dielectric permittivity (e) is fixed as 9. The desired focus, also the geometric focus, is at z=6 cm. While the electric field can be focused for tissue conductivities less than 0.3, it decreases monotonically along z-axis for higher tissue loss (s=0.5). In FIG. 9B, the electric field distribution for higher tissue dielectric permittivity is shown. Shown in the figures are the absolute values of the electric field for an input voltage of 1 V.

The electric field intensities along the z-axis for $\varepsilon_r$=9 and for various values of $\sigma$ are plotted in 1 cm steps from the surface to the target in FIG. 9A. It can be seen clearly that the field has its maximum at the second focus. However, this focusing effect diminishes as the conductivity increases from 0.3 S/m to 0.5 S/m: the maximum field is located on the surface and it decreases monotonically on the z-axis. The decreasing trend of the z-axis electric field however is reversed when the tissue permittivity was changed from 9 to 70, as shown in FIG. 9B. With the tissue dielectric permittivity of 70, the field is focused at the geometric focus even for a conductivity of 1 S/m. Clearly, the focusing effect is more pronounced in tissue with higher permittivity.

Figure 10:
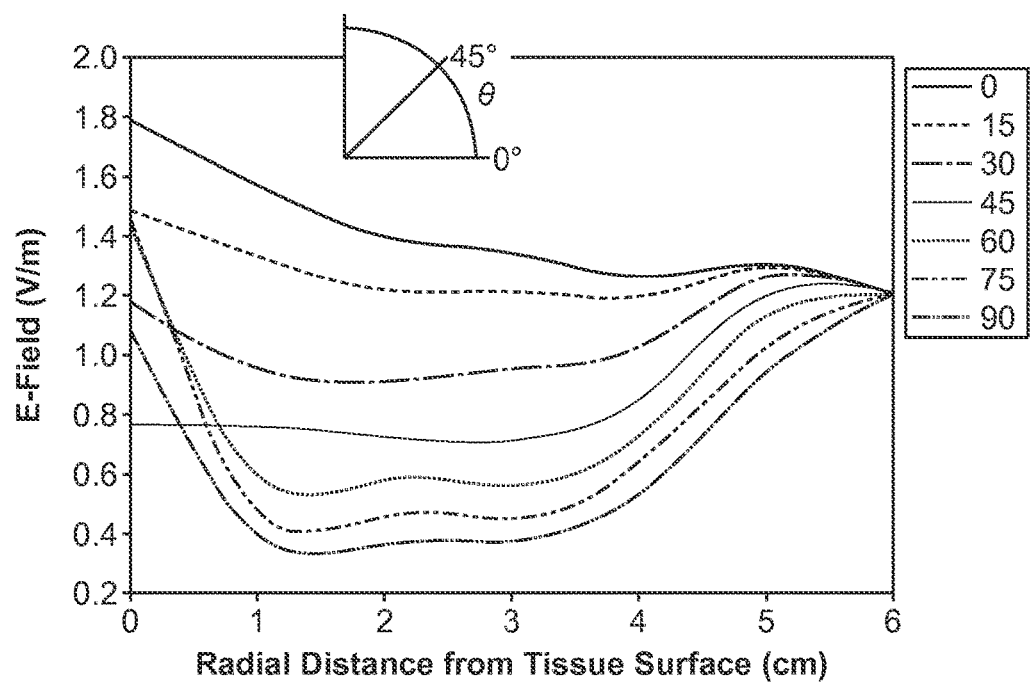
FIG. 10 shows a plot of the field distribution in the radial direction at different angles θ.

The field distribution in the radial direction at different angles θ is shown in FIG. 10. FIG. 10 shows the electric field distribution in the radial direction at different azimuthal angles (θ). At the surface of the tissue hemisphere, the highest electric field is near the z-axis, but it decreases to 60% at the geometric focus. In other radial paths with angles greater than 30°, the field at the surface is either approximately equal or smaller than the field at the geometric focus. The tissue has dielectric permittivity ($\varepsilon$=9) and conductivity ($\sigma$=0.5).

In this case, the tissue dielectric constant is 9 and the conductivity is 0.5 S/m. The electric field amplitudes on the z-axis as well as those of the electromagnetic wave with a small azimuthal angle) (<30°) in the radial direction show a decreasing trend as they propagate into the tissue. On the other hand, the waves traveling in the radial direction with larger angles decrease over the first 1-2 cm, but increase eventually at the destination (6 cm in depth). The differences in losses along different radial paths suggest the possibility to generate a focal spot in the deeper tissue by attenuating the electric fields on or near the z-axis, and letting only the electric fields along paths of wider angles continue to propagate. As will be shown below, this can be achieved by manipulating the properties of the lens.

In order to maximize the electrical energy density in a focal spot in the deep tissue, two conditions need to be satisfied. First, as briefly discussed above, the amplitude of the electromagnetic wave at small angles needs to be attenuated, and secondly, the reflection loss due to the abrupt change in tissue permittivity at the interface of air and tissue needs to be minimized. These two conditions led us to use an inhomogeneous, partially lossy dielectric lens. In a previous paper[16], it was already shown that a multilayer dielectric lens can be used to match the impedance from air to tissue. The lens consists of five layers of different dielectric materials with dielectric constants varying in an exponential profile from air to the innermost layer, $\varepsilon_{max}$. Due to the increase of the dielectric constant, the focal spot size can be reduced by a factor of $\varepsilon_{rmax}^{-1/2}$ at the innermost layer, and the electric field can be enhanced by a factor of $\varepsilon_{max}^{1/4}$. The choice of the number of layers and their thickness was optimized to permit maximal transmission through these layers. Here, a similar lens was used, but with two major differences: 1) tissue with a given conductivity was inserted into the innermost layer; and 2) the innermost layer and the second to the last layer of the lens were made lossy for angles below 45°, which means, for azimuth angles between −45° and +45°, it has a finite conductivity (1 S/m or 2 S/m). The dielectric constants of the materials were kept the same as in the previous lens design. With this design, the electric field distribution has been simulated for the cases where the lens does and does not include lossy layers.

Figure 11:
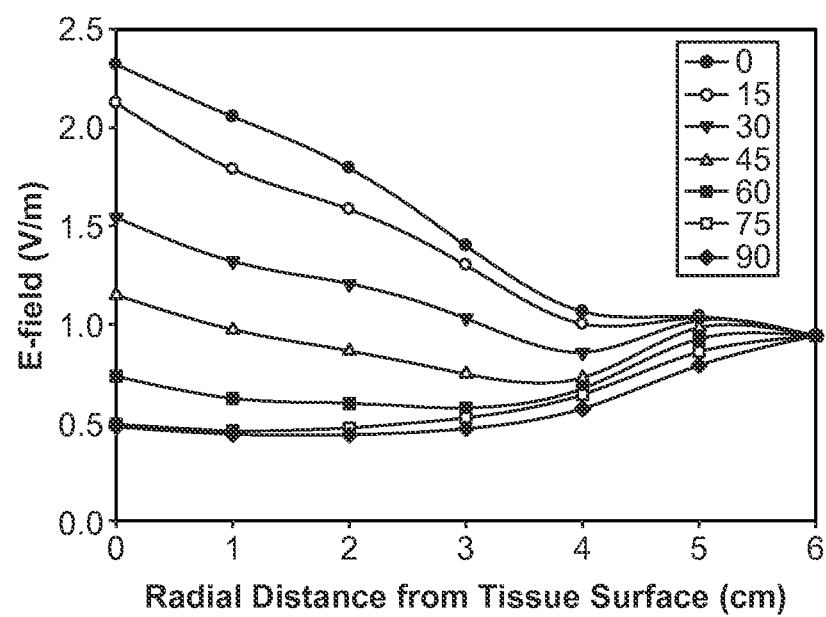
FIG. 11 shows a plot of the field distribution of impulse for tissue conductivity of 0.5 S/m when the lens has no lossy layers.
Figure 12A:
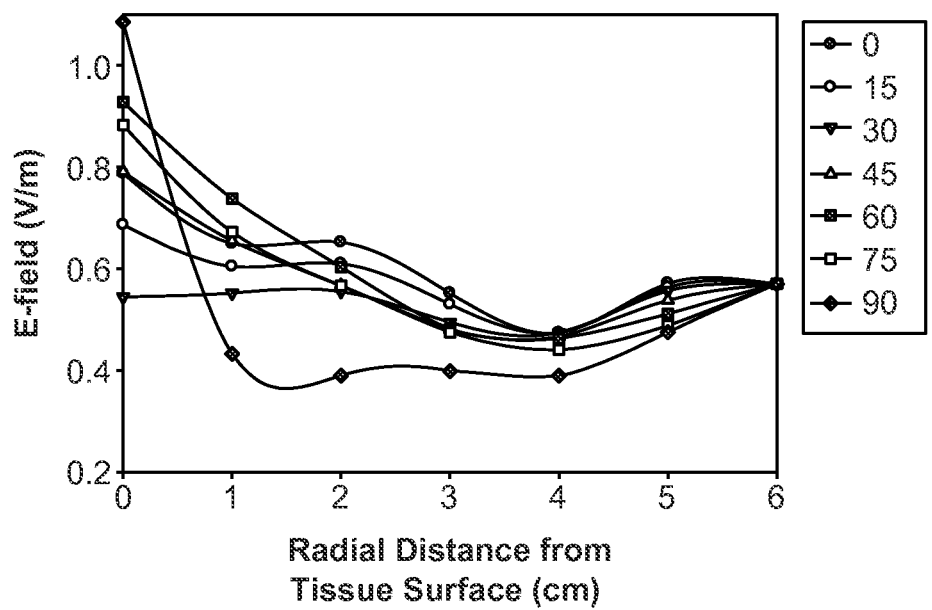
FIG. 12A shows a plot of the electric field distribution along paths at different azimuth angles when a partially lossy lens is used in addition to the reflector antenna and where the conductivities of the last two layers of the lens are 1 S/m.
Figure 12B:
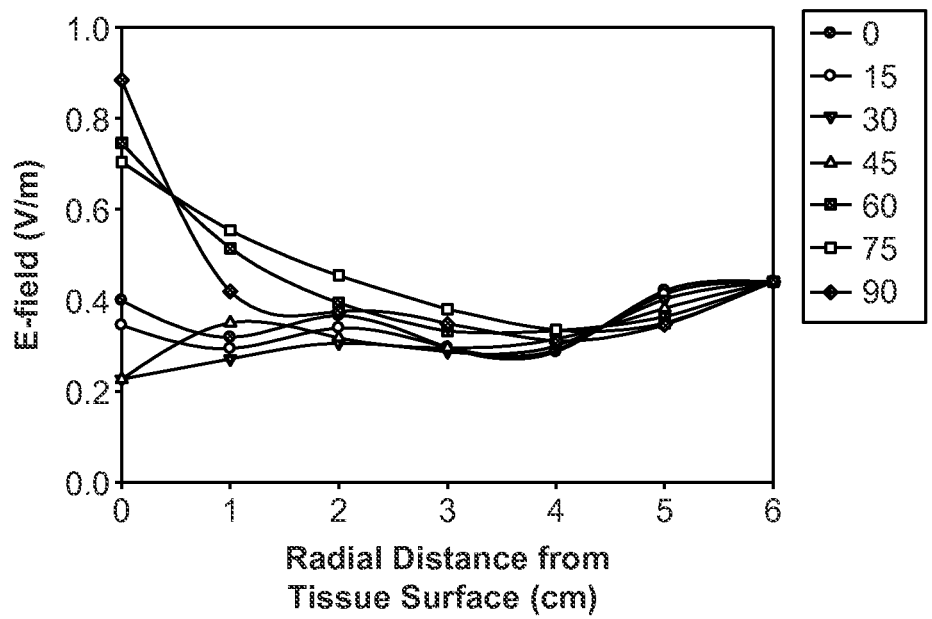
FIG. 12B shows a plot of the electric field distribution along radial paths when the conductivities of the last two layers are 1 S/m and 2 S/m.

FIG. 11 shows the field distribution of impulse for tissue conductivity of 0.5 S/m when the lens has no lossy layers. On the z-axis, the electric field decreases steadily as the distance increases from the surface. For paths of larger angles, there is an increase as the distance increases. In the case where two layers were made lossy (1 S/m for both layers), the field distribution is changed (FIG. 12A) due to the strong attenuation of the lossy layer, the field distribution (for example θ=0°, 30° becomes lower on the surface than for the case where there are no lossy layers in the lens. The field intensity on the surface at larger angles becomes larger. But overall, the fields along all radial paths show a decreasing trend as the distance increases. However, when the conductivity of the second last layer is increased from 1 S/m to 2 S/m, the electric field intensity on the z-axis becomes smaller on the surface, but increases at a depth of 6 cm (FIG. 12B). Meanwhile, the radial distributions along other radial paths near the z-axis also show a slight increase in the deeper area, except on the surface of the tissue at angles >60°. We note that such distribution is for the tissue conductivity of 0.5 S/m, and for the tissue conductivity of 1 S/m, a similar field distribution was obtained. The field distribution can be schematically shown in FIG. 13A. In the case of a non-lossy lens, the field distribution can be schematically depicted by the pie-shaped distribution in FIG. 13B. A comparison of FIGS. 13A and 13B shows a localized focus may be formed in the deep region of the tissue. This change in distribution is made at the cost of the reduction of the absolute field intensity at the targeted region and two extra "hot spots" near the surface.

It has been shown above that it is possible to confine the electric field of subnanosecond pulses in a homogeneous, dielectric hemisphere. The attenuation loss of the target can be offset by using a partially lossy lens so that a deep-seated focal region can be created. While the targeted hemisphere is simple in structure, a real tissue contains multiple tissue layers, making the formation of a focal spot more challenging. Three cases have been investigated: 1) the subnanosecond pulses are directed to the brain by the ellipsoidal reflector only; 2) a lens is placed on top of a human head; and 3) the lens is made partially lossy in order to attenuate the field along the axis. The lens, with the same structure as in FIG. 3, is used with the antenna and placed on top of the human head, as illustrated in FIGS. 2A and 2B. The dielectric constant of each layer was the same as in FIG. 3. Because the head is not exactly round in shape, the top of the head coincides with the lens axis. So the head appears to project into the lens structure. But at the lens-head interface, the priority is given to the head, which overrides the lens in any overlapped region. For the lossy lens, which is similar to the lens used in Section 3.2, the innermost layer is assigned a conductivity of 5 S/m and the second-last layer is assigned a conductivity of 4 S/m. The values of the conductivities were selected based on the consideration that the electric field on the axis increases as the wave penetrates deeper and nears the geometric focus. However, that does not mean that the electric fields in other radial paths of the penetration are lower than the fields near the geometric focus, as will be shown later.

First examined is the case where the pulse is directly (without lens) delivered to the brain through the impulse radiating antenna. FIG. 14 shows the pulse waveform at the geometric focus in the brain (6 cm deep from the top of the skull). Again, the y-component dominates the overall field and the x and z components are negligible.

Figure 15:
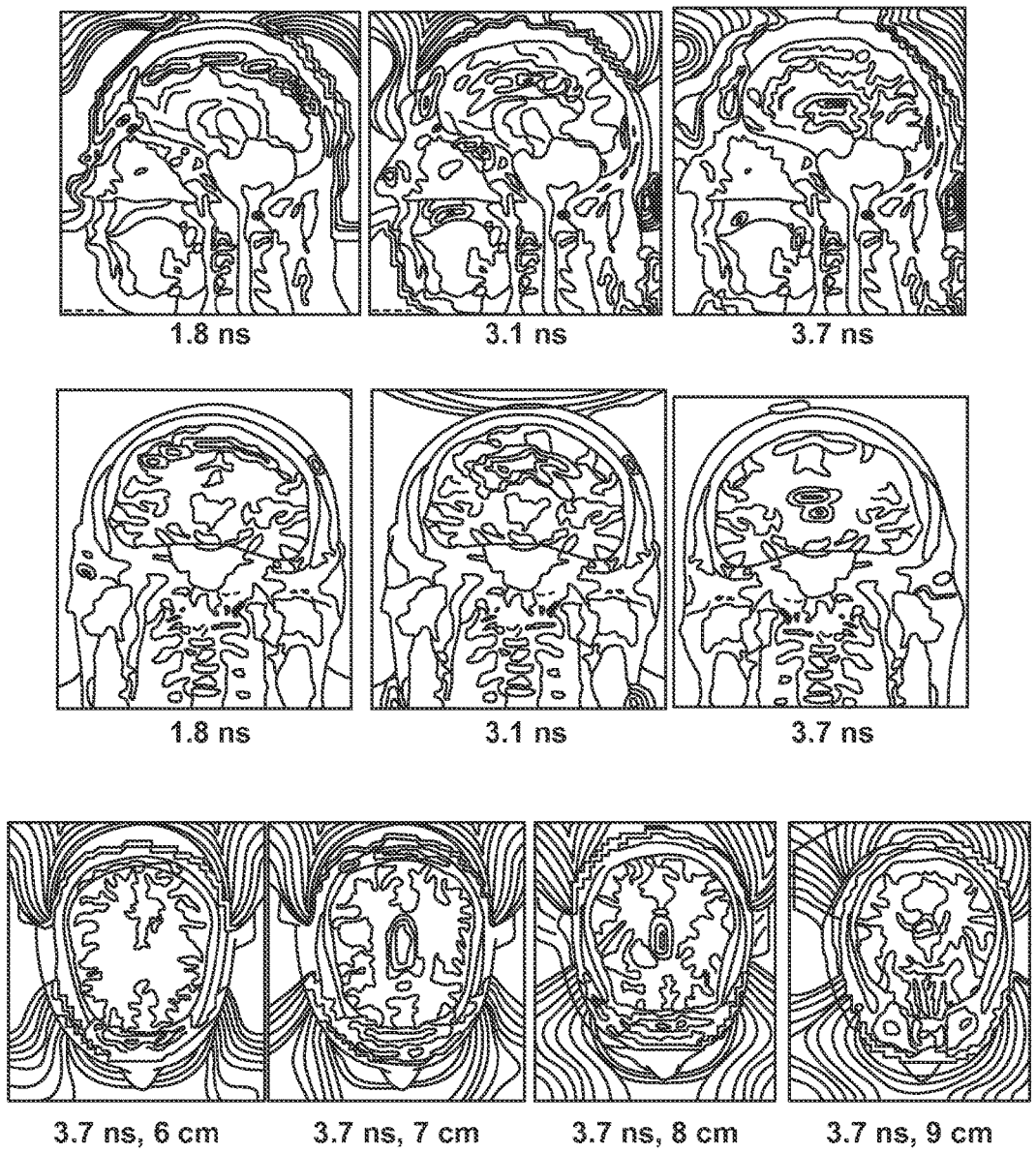
FIG. 15 shows the isoline plots of electric field distribution in the human brain without a dielectric lens at various times with a clamp to range of 0.1 to 0.3 along the X axis (side view), Y axis (back view) and Z axis (top view), where the top-view slice is taken along the plane of the lens at 6, 7, 8 and 9 cm deep in a human head.

FIG. 15 shows the propagation of subnanosecond pulses in the head. In particular, FIG. 15 shows isoline plots of electric field distribution in the human brain without a dielectric lens at various times (1.8 ns to 3.7 ns), where the top, middle, and bottom rows are view along the X-axis (side view), Y-axis (back view), and Z-axis (top view), respectively. The intensity of the electric fields is shown as the linear isoline in the clamped range 0.1-0.3 V/m, meaning any values that are greater than 0.3 are clamped to 0.3. At 1.8 ns, the prepulse already reaches the brain. In the meantime, the prepulse in the face and back side of the head travels faster than the prepulse in the brain. At 3.1 ns, the impulse appears in the brain along the axis of the antenna. It gradually reduces its size and at 3.7 ns, seems at its smallest size. As the wave penetrates deeper, the intensity decreases. The isoline plot clearly indicates that there is no resonance in the brain except the impulse. In the back view of the wave propagation (FIG. 15), at 3.1 ns, one can see that the impulse actually consists of two parts indicated by two bright spots. In the time domain, the corresponding impulse waveform is bipolar (FIG. 14). At 3.7 ns, the wave converges, which is consistent with the side view. A top view of the wave propagation is also shown in FIG. 15 in the bottom row. The Z-axis views are taken at depths of 6, 7, 8 and 9 cm from the top of the head. Because the wave intensity is shown as a clamped isoline, a number of probes were placed in the brain to measure the actual peak amplitudes as the pulse passes. The probes were placed in 1 cm steps along the radius centered at the second geometric focal point, which is 6 cm deep from the top of the skin fat.

Figure 16:
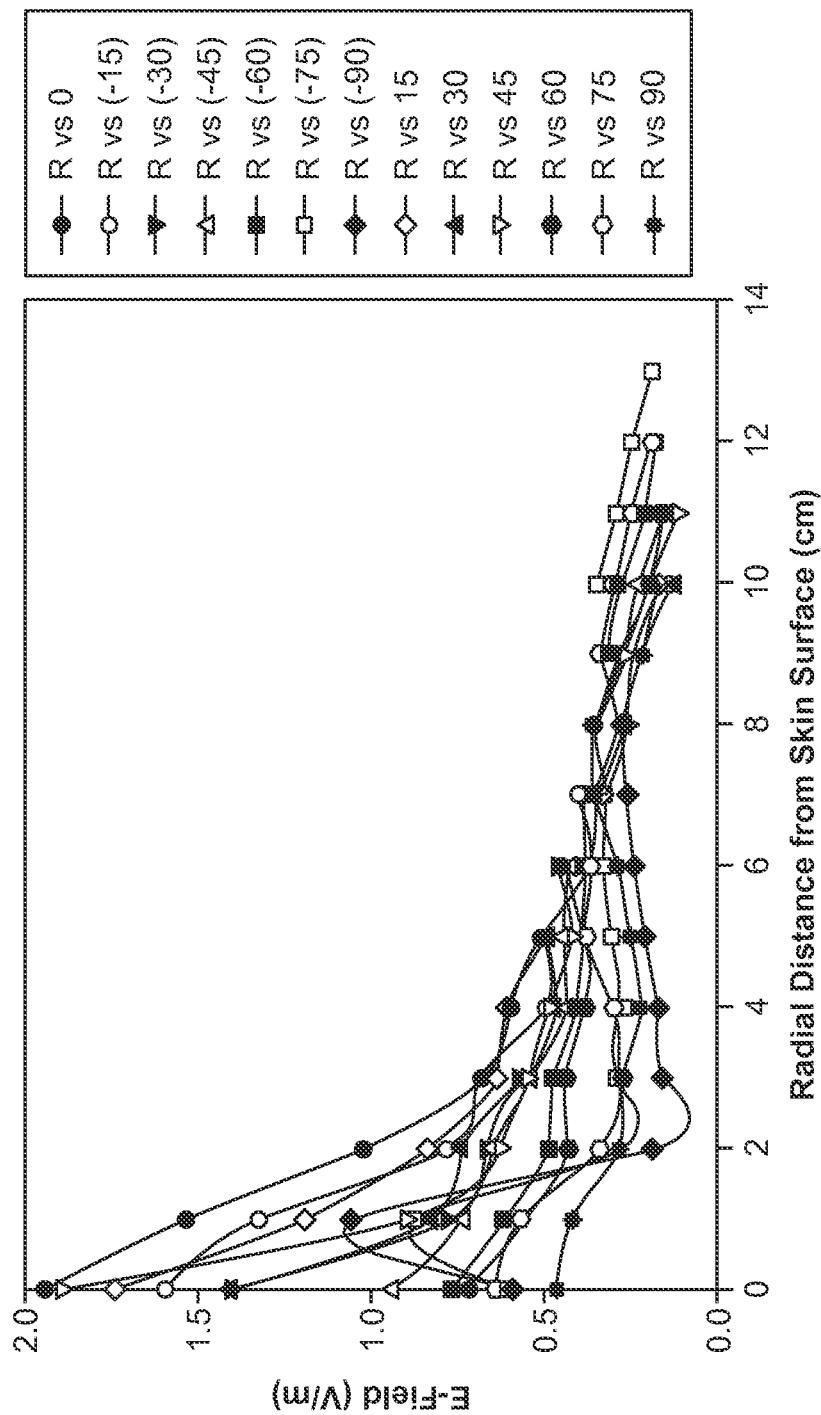
FIG. 16 is a plot of the electric field distribution in the brain exposed to the reflector antenna without the dielectric lens.

FIG. 16 shows the field distribution along various radii from the skin. The largest field is on the axis (0°) and the fields on the two sides seem symmetrical about the axis. They all decrease due to the strong absorption in the brain. Despite the fact that the field decreases as the penetration depth increases, the field values converge at 7-8 cm, a sign of geometric focusing in the space, which is also consistent with the results shown in FIG. 15. The inhomogeneity of the brain does not seem to create any difference in the arrival time of the spherical waves along different radii, but the strong attenuation of brain tissue prevents the wave from reaching the highest amplitude near the focal point.

Figure 17:
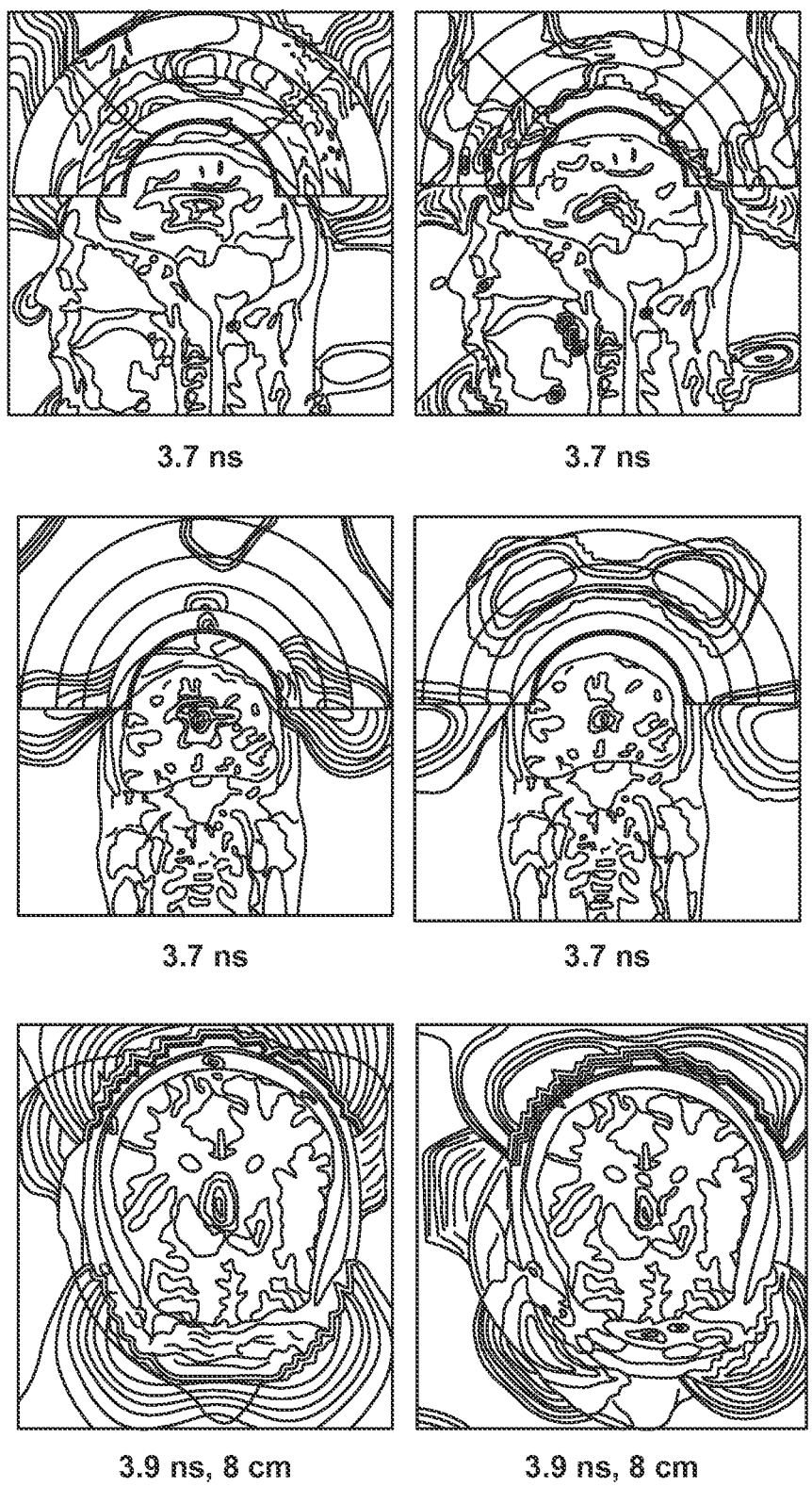
FIG. 17 shows the isoline plots of electric field distribution of the human brain with a dielectric lens according to the various embodiments at various times along the along the X axis (side view), Y axis (back view) and Z axis (top view), where the top-view slice was taken along the plane at 8 cm deep in a human head.

FIG. 17 shows the isoline plots of electric field distribution of the human brain under a dielectric lens at various times along the X-axis (side view), Y-axis (back view), and Z-axis (top view), shown in the top, middle, and bottom rows, respectively. The top-view slice was taken along the plane at 8 cm deep in the head. The left panel is for the non-lossy lens and the isoline plot has a clamp to range of 0.1 to 0.5 V/m. The right panel is for the lossy lens and the isoline plot has a clamp to range of 0.1 to 0.2 V/m.

Figure 18:
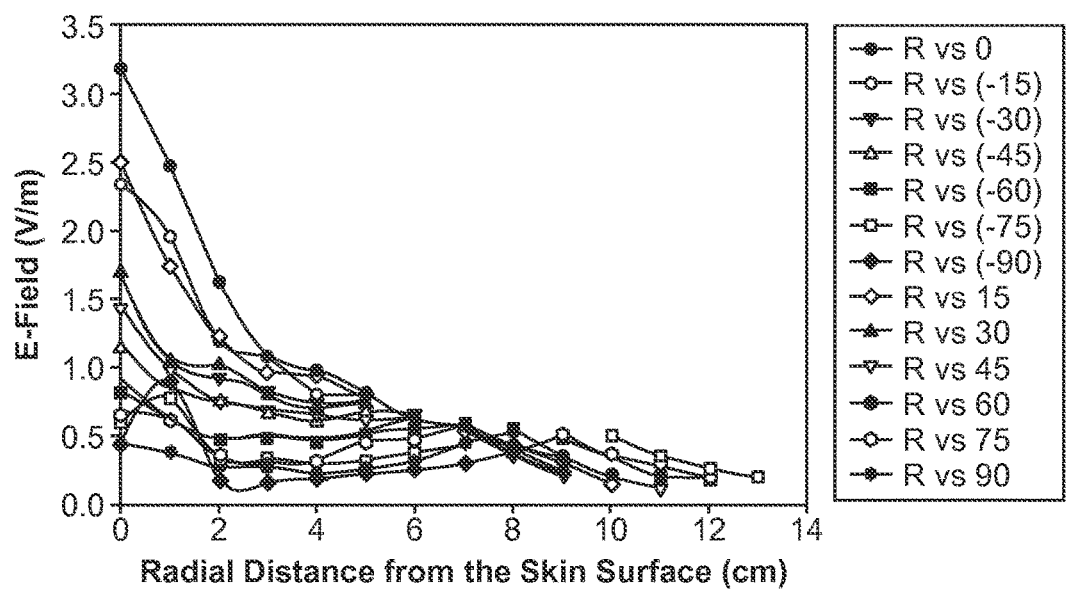
FIG. 18 shows a plot of the electric field distribution in the brain with the non-lossy lens.

For a non-lossy lens placed on top of the head, the resulting field distribution in isoline plots are shown in the left panels of FIG. 17. In this case, the isoline was clamped between 0.1-0.5 V/m. At 3.7 ns, the impulse becomes constricted in size and it reaches 8 cm deep at 3.9 ns. After that, the impulse decreases in intensity and becomes almost invisible in the clamped range. The addition of the lens creates a delay compared with the case without a lens. The amplitudes of the field are shown in FIG. 18. The field distribution is similar to the case where there is no lens added, except the amplitude at the skin is slightly higher due to the higher transmission of the lens. The field values converge to 0.5 V/m at the depth of 8 cm. Still, the highest field is on the axis and the fields on both sides are smaller. The overall trend is decreasing as the impulse penetrates.

Figure 19:
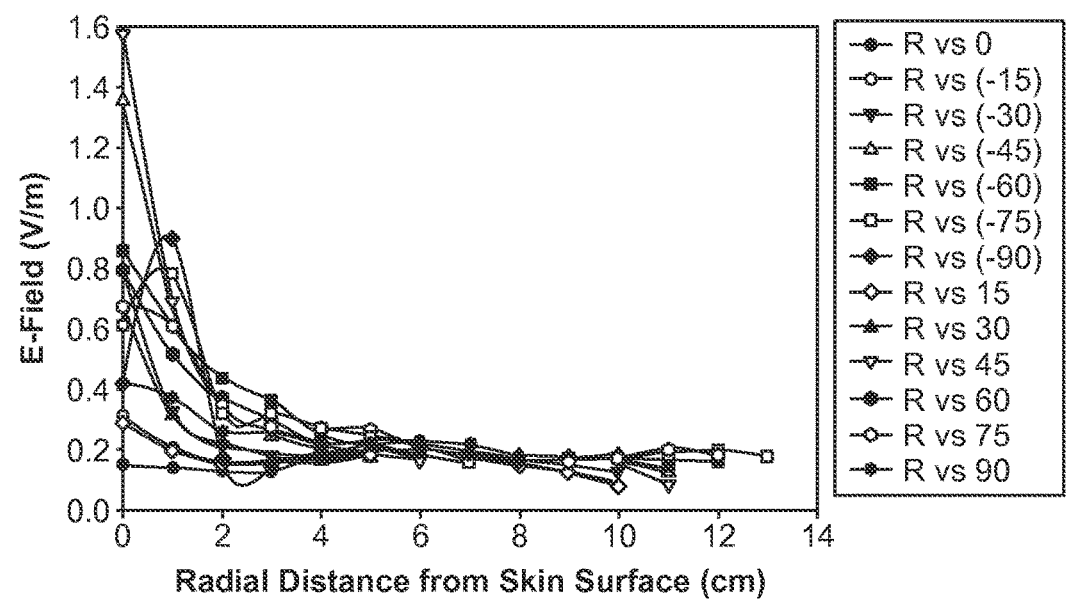
FIG. 19 shows a plot of the electric field distribution in the brain with the lossy lens.

For a lossy lens placed on top of the head, the resulting field distribution in isoline plots are shown in the right panels of FIG. 17. In this case, the field on the axis is attenuated by assigning conductivities to the 4th and 5th layer of the lens. In the side view of the wave propagation (FIG. 17, right panel, first row), the impulse field, shows a "wishbone-like" distribution (at 3.7 ns). At 3.9 ns, the impulse is confined at 8 cm from the top of the skull. In FIG. 19, the field distribution is shown. On the axis (R vs 0°), the field becomes the lowest among all the radial directions and is slightly increased at a 8 cm, which is the opposite of that in FIG. 16 and FIG. 18, where the largest field is on the axis. The fields at ±45° become the largest. The strong attenuation in the lossy lens allows us to modify the field distribution in the brain. Despite the strong attenuation, the field intensity near the focal point (6-8 cm in depth) is 0.2 V/m, reduced by a factor of three from that in the non-lossy lens case (FIG. 18).

When sending subnanosecond pulses to a tissue, such as brain tissue, using an impulse antenna, a spherical wave with a propagation vector perpendicular to a spherical target converges on the geometric center of the spherical wave. This offers a rather simple prediction of the field distribution in the target. The conductivity of the tissue however changes the geometric-optics picture. It creates a decreasing electric field with increasing penetration distance. For the generation of large field intensities in the shallow region of the brain, a single antenna is sufficient. As the antenna radiation is an inhomogeneous spherical wave, the highest field is along the axis, which means the highest field distribution in the target also coincides with the axis. For deeper focusing, the loss due to the conductivity of the dielectric can be alleviated by applying this method to tissue with high dielectric constants, such as muscle tissue.

In a target which contains composite tissues, such as the brain in this study, the multiple layers in the propagation path (skin and skull) do not pose a significant change to the waveforms of the converging waves, since, in FIG. 14, both prepulse and impulse can be clearly identified. In addition, the focal spot size in the brain is mainly determined by the white matter, where the spherical wave converges. As white matter has a dielectric constant of 37, the spatial width of such pulse is 1 cm. The simulation shows that the spot size is on the order of 2 cm for input pulse duration of 200 ps. It is therefore reasonable to predict the focal spot size simply by estimating the pulse spatial width in the dielectric where the focal point is to be created.

The electric field distribution obtained in a hemispherical tissue (FIGS. 11 and 12B) and a brain model (FIGS. 18 and 19) demonstrates two extreme cases of electric field distributions. One has the highest field on the z-axis while the fields on the side are small. This case creates a field distribution without a deep maximum. The other case is that high fields penetrate from the two sides about the z-axis, while leaving the axial field small, but in the deep region, a local maximum can be formed. The first case can be used for delivering subnanosecond pulses to the shallow regions along the axis and the second case can be used for delivering subnanosecond pulses to the shallow region on the sides. The targeted region can be selected by placing lossy materials in the corresponding incident angles of the lens, which offers one way of varying the focal zone—by utilizing different lenses. On the other hand, the second case suggests that it may be possible to focus the pulse in deep regions and reduce the fields on the sides. This could be done by optimizing the configuration of the lens. Such a lens could consist of a number of lossy elements in the same layer of the lens with each layer having different values of conductivities. A typical multi-variable optimization method, such as a generic algorithm[30], can be used to find the optimum values of the lens segments.

Previous studies of the biological effects near 1 ns mostly were focused on the electric field range, 16-250 kV/m[21]. The findings reported were mostly negative. Various aspects, including regulation of heart rate and blood pressure[22, 23], chemically induced convulsions[24], and behavior, hematology, and brain histology[25], showed no response to the short pulses. A behavioral study in primates[26], and yeast[27], also did not show any effects.

In these physiological studies, the electric fields were presumably low. When the electric field strengths were increased by 10-fold, up to 1.2 MV/m, muscle stimulation became feasible, as shown in a later study[21]. Even single 1 ns pulses with electric field strength 1.2 MV/m were able to stimulate frog gastrocnemius muscles. The strength duration curve (S-D curve) from 1 ms to 1 ns showed a linear trend, which suggests the feasibility of stimulating excitable tissue into the subnanosecond (picoseconds) range. A recent study[28] using longer pulses (12 ns) also showed that single electric pulses were able to elicit action potentials when the pulses were applied to rat skin nociceptors. The critical electric field strength of 403 V/cm was found to be dependent on the frequency and burst duration. When the electric pulses were applied in a repetitive, burst manner, the electric field strength threshold of stimulation was reduced to 16 V/cm for a 4 kHz, 25 ms burst.

Using the same linear scaling of Rogers et al.[21], one can extrapolate the critical electric field for stimulation with 200 ps to be 6 MV/m. An estimate within an order of magnitude can be made to be 1 MV/m-10 MV/m. On the other hand, as Jiang and Cooper showed[28], the critical electric fields may decrease by a factor of 20 if the pulses are delivered at a high rep-rate (4 kHz). Therefore, an electric field of 50 kV/m and 500 kV/m may be sufficient for stimulation. These values are within the capability of antenna delivery. As shown in FIG. 16 and FIG. 18, for a voltage of 1 V fed to the antenna, an electric field is in the range of 1.5 V/m at a depth of 2 cm, which is the motor cortex region in the brain. This means an input voltage from 33.3 kV to 333 kV may be enough for an effective stimulation. For deep stimulation, FIG. 11, FIG. 13 and FIG. 14 indicate there is a locally focused region at a depth of 7-8 cm. For a 1V pulse input, the field intensity was found to be 0.2-0.5 V/m for the three cases, which suggests that pulses of 250 kV-2.5 MV need to be fed into the antenna in order to meet the estimated minimum stimulation threshold of 50 kV/m. Such a high-amplitude pulse generator becomes technically challenging (if not impossible) even though a 1 MV pulse generator has been built[31].

In summary, the electric field distribution shows a steadily decreasing trend and is primarily caused by the tissue conductivity. But increasing the tissue dielectric constant, meaning applying the method to a different tissue, can reverse the trend and allows for a deep focusing (6 cm in depth for example). A second approach that could possibly create deep focusing is to use a dielectric lens in conjunction with the antenna. The lens can modify the electric field distribution in the tissue. In one case, the lens is loss-free and the electric fields along the axis are the highest. In the other case, the lens is assigned with lossy material to attenuate the axial incident electric fields, but allowing the incident fields from the sides to pass. This case results in the opposite distribution as the first case: the largest fields on the side, and the small fields along the axis. A local maximum near the geometric focus exists in this case. When the target is replaced by a human brain, the field along the axis is still strongest if the human head is directly exposed to the antenna. Despite a slight asymmetry of the human head, the spherical wave still converges near the geometric focus. However, the overall intensity decreases from the surface as the wave penetrates, due to a strong resistive loss of the tissue. Adding a dielectric lens allows one to increase the field intensity near the geometric focus, but the strongest intensity is still found along the axis and decreases as the wave penetrates deeper. When the lens is made lossy, the field on the axis can be adjusted to the lowest in the brain, while leaving the field distribution near the ±45° largest. This study suggests the possibility of designing a dielectric lens with heterogeneous distribution of lossy material to create a desirable electric field distribution in the brain, perhaps even allowing for deep-focusing. Future work will be embedding lossy elements to the lens layers and steering the antennas to move the focal point in the brain.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

REFERENCES

The following references describing information for understanding the various embodiments of the invention. Each of these references is herein incorporated by reference in their entirety.

[1] Attal, N., Cruccu, G., Haanpaa M., et al., "EFNS guidelines on pharmacological treatment of neuropathic pain," Eur J Neurol 13 1153-1169 (2006).
[2] Brown, J. A., "Motor cortex stimulation," Neurosurg Focus 11: E5, (2001).
[3] Cruccu, G., Aziz, T. Z., Garcia-Larrea, L., Hansson, P., Jensen, T. S., Lefaucheur, J.-P., Simpson, B. A. and Taylor, R. S., "EFNS guidelines on neurostimulation therapy for neuropathic pain," European Journal of Neurology 14, 952-970 (2007).
[4] Rudiak, D. and Marg, E., "Finding the depth of magnetic brain stimulation: a reevaluation," Electroencephalogr. Clin. Neurophysiol. 93, 358-371 (1994).
[5] Jun, S. B., "Ultrasound as a Noninvasive Neuromodulation Tool," Biomed Eng Lett 2, 8-12, DOI 10.1007/s13534-012-0050-2 (2012).
[6] Gavrilov, L. R., "Use of focused ultrasound for stimulation of nerve structures," Ultrasonics 22, 132-8 (1984).
[7] Clement, G. T. and Hynynen, K., "A noninvasive method for focusing ultrasound through the human skull," Phys. Med. Biol. 47, 1219-1236 (2002).
[8] Zhang, F., Gradinaru, V., Adamantidis, A. R., Durand, R., Airan, R. D., de Lecea, L. and Deisseroth, K., "Optogenetic interrogation of neural circuits: technology for probing mammalian brain structures," Nat Protoc. 5, 439-56 (2010).
[9] Ryan, T. P., Trembly, B. S., Roberts, D. W., Strohbehn, J. W., Coughlin and C. T., Hoopes, P. J., "Brain hyperthermia: I. Interstitial microwave antenna array techniques—the Dartmouth experience," Int J Radiat Oncol Biol Phys 29, 1065 (1994).
[10] Dunn, D., Rappaport, C. M. and Terzuoli. Jr, A. J., "FDTD verification of deep-set brain tumor hyperthermia using a spherical microwave source distribution," IEEE Trans. MTT 44, 1769-77 (1996).
[11] Gouzouasis, I. A., Karathanasis, K. T., Karanasiou, I. S. and Uzunoglu, N. K., "Contactless passive diagnosis for brain intracranial applications: a study using dielectric matching materials," Bioelectromagnetics 31, 335-349 (2010).
[12] Burfeindt, M. J., Zastrow, E., Hagness, S. C., Van Veen, B. D. and Medow, J. E., "Microwave beamforming for non-invasive patient-specific hyperthermia treatment of pediatric brain cancer," Physics in Medicine and Biology 56, 2743(2011).
[13] Xiao, S., Altunc, S., Kumar, P., Baum, C. E. and Schoenbach, K. H., "A reflector antenna for focusing in the near field," IEEE Antennas and Wireless Propagation Letters 9, 12-15 (2010).
[14] Bajracharya, C., Xiao, S., Baum, C. E. and Schoenbach, K. H., "Target detection with impulse radiating antenna," IEEE Antennas and Wireless Propagation Letters 10, 496-499 (2011).
[15] Kumar, P., Baum, C. E., Altunc, S., Buchenauer, J., Xiao, S., Christodoulou, C. G., Schamiloglu, E. and Schoenbach, K. H., "A hyperband antenna to launch and focus fast high-voltage pulses onto biological targets," IEEE Trans. Microwave Theory and Techniques 59, 1090-1101 (2011).
[16] Altunc, S, Baum, C. E., Christodoulou, C. G., Schamiloglu, E. and Buchenauer, C. J., "Focal waveforms for various source waveforms driving a prolate-spheroidal impulse radiating antenna (IRA)," Radio Sci. 43: RS4S13 (2008).
[17] Lazebnik M, Popovic D, McCartney L, Watkins C B, Lindstrom M J, Harter J, Sewall S, Ogilvie T, Magliocco A, Breslin A T M, Temple W, Mew D, Booske J H, Okoniewski M, Hagness S C. 2007. A large-scale study of ultrawideband microwave dielectric properties of normal, benign and malignant breast tissues obtained from cancer surgeries. Phys. Med. Biol. 52:6093-6115.
[18] Gabriel C, 2007. Dielectric Properties of Biological Material. Handbook of Biological Effects of Electromagnetic Fields, 3$^{rd}$ Edition, Edited by F. S. Barnes and B. Greenebaum, CRC press.
[19] Lin J C, Bernardi P. 2007. Computational methods for predicting field intensity and temperature change. In Barnes F S, Greenebaum B (eds): Handbook of Biological Effects of Electromagnetic Fields, 3rd Edition, Edited by, CRC press.
[20] Baum C E. 2007. Focal waveform of a prolate-spheroidal impulse-radiating antenna (IRA). Radio Sci. 42: RS6S27.
[21] Rogers W R, Merritt J H, Comeaux J A Jr., Kuhnel C T, Moreland D F, Teltschik D G, Lucas J H, Murphy M R. 2004. Strength-duration curve for an electrically excitable tissue extended down to near 1 nanosecond. IEEE Transactions on Plasma Science 32:1587-1599.
[22] Jauchem J R, Seaman R L, Lehnert H M, Mathur S P, Ryan K L, Frei M R, Hurt W D. 1998. Ultra-wideband electromagnetic pulses: lack of effects on heart rate and blood pressure during two-minute exposures of rats. Bioelectromagnetics. 19:330-333.
[23] Jauchem J R, Frei M R, Ryan K L, Merritt J H, Murphy M R. 1999. Lack of effects on heart rate and blood pressure in ketamine-anesthetized rats briefly exposed to ultra-wideband electromagnetic pulses. IEEE Trans. Biomed. Eng. 46:117-120.
[24] Miller S A, Bronson M E, Murphy M R. 1999. Ultrawideband radiation and pentylenetetrazol-induced convulsions of rats. Bioelectromagnetics 20: 327-329.
[25] Walters T J, Mason P A, Sherry C J, Steffen C, Merritt J H. 1995. No detectable bioeffects following acute exposure to high peak power ultra-wide band electromagnetic radiation in rats. Aviat. Space Environ. Med. 66: 562-567.
[26] Sherry C J, Blick D W, Walters T J, Brown G C, Murphy M R. 1995. Lack of behavioral effects in non-human primates after exposure to ultrawideband electromagnetic radiation in the microwave frequency range. Radiat. Res. 143: 93-97.
[27] Pakhomova O N, Belt M L, Mathur S P, Lee J C, Akyel Y. 1988. Ultra-wideband electromagnetic radiation does not affect UV-induced recombination and matagenesis in yeast. Bioelectromagnetics 19:128-130.
[28] Jiang N, Cooper B Y. 2011. Frequency-dependent interaction of ultrashort E-fields with nociceptor membranes and proteins. Bioelectromagnetics 32:148-163.
[29] Altunc S, Baum C E, Christodoulou C G, Schamiloglu E, Buchenauer C J. 2009. "Design of a special dielectric lens for concentrating
[30] Pham D T, Karaboga D. 2000. Intelligent Optimisation Techniques. Springer, London.
[31] Baum C E, Baker W L, Prather W D, Lehr J M, O'Loughlin J P, Giri D V, Smith I D, Altes R, Fockler J, McLemore D, Abdalla M D, Skipper M C. 2004. JOLT: a highly directive, very intensive, impulse-like radiator. Proceedings of the IEEE 92(7):1096-1109.
[32] Vitek J L, DeLong M R, Starr P A, Hariz M I, Metman L V. 2011. Intraoperative neurophysiology in DBS for dystonia. Movement Disorders 26: 31-36.

What is claimed is:
1. A system configured to deliver electric pulses to a targeted region within a biological tissue, comprising:
an antenna assembly configured to generate and direct electromagnetic radiation;
a lens configured to be positioned between a surface of the biological tissue and the antenna assembly, the lens having a plurality of lossy portions;
wherein the lens is configured to be adjustable to create a patient-specific desired electric field distribution by selective positioning of the plurality of lossy portions within the lens.
2. The system of claim 1, wherein the lens comprises a plurality of layers, each layer having a different value of conductivity.
3. The system of claim 2, wherein the plurality of lossy portions is positioned within a single layer of the plurality of layers.
4. The system of claim 2, wherein the plurality of lossy portions is positioned within multiple layers of the plurality of layers.
5. The system of claim 1, wherein the plurality of lossy portions is positioned at various incident angles of the lens.
6. The system of claim 1, wherein each of the plurality of lossy portions is configured to attenuate a portion of the electromagnetic radiation traveling in at least one direction.
7. The system of claim 1, wherein the targeted region is a deep tissue region of the biological tissue and wherein the system is configured to increase a transmission of the electromagnetic radiation to the deep tissue region of the biological tissue.
8. The system of claim 7, wherein a focal spot in the deep tissue region is generated by attenuating the electric fields on or near a z-axis.
9. The system of claim 1, wherein the deep tissue region comprises a region of 6 to 8 cm below a surface of the biological tissue.
10. The system of claim 1, wherein the system configuration simultaneously targets both deeper and shallower regions of the biological tissue.
11. The system of claim 1, wherein the electromagnetic radiation from the antenna assembly is configured to enter the targeted tissue at wide angles.

12. The system of claim 11, wherein the wide angles are equal or greater than 45 degrees.

13. The system of claim 1, wherein the antenna assembly comprises a wide-band antenna configured to provide wide and narrow angles.

14. The system of claim 1, further comprising a pulse generator coupled to the antenna assembly and configured for generating a series of pulses.

15. The system of claim 14, wherein the pulse generator is configured for generating a pulse having a pulse duration of less than or equal to 1 ns.

16. The system of claim 14, wherein the pulse generator is configured for generating a pulse having a magnitude between about 1 kV and 1 MV and a repetition rate between about 1 Hz and 1 MHz.

17. The system of claim 1, wherein at least one of a rise time or a fall time of the electric pulses is from 1 ps to 1 ns.

18. The system of claim 1, wherein the lens comprises a plurality of layers and at least one of a radius, thickness, or dielectric constant of each layer of the plurality of layers varies.

19. The system of claim 1, wherein the antenna assembly comprises an antenna configured for receiving the electric pulses and generating the electromagnetic radiation and a reflector configured for directing the electromagnetic radiation to the lens.

20. The system of claim 1, wherein the lens is shaped and configured for positioning adjacent to the biological tissue and a dielectric constant of a surface of the lens that is adjacent to the biological tissue substantially matches a dielectric constant of the biological tissue.

* * * * *